(12) United States Patent
Apostolos et al.

(10) Patent No.: US 9,170,311 B2
(45) Date of Patent: Oct. 27, 2015

(54) NUCLEAR QUADRUPOLE RESONANCE SYSTEM

(71) Applicant: AMI Research & Development, LLC, Windham, NH (US)

(72) Inventors: John T. Apostolos, Lyndeborough, NH (US); William Mouyos, Windham, NH (US); Brian Molen, Windham, NH (US); Kurt Colon, Rockaway, NJ (US); Judy Feng, Nashua, NH (US); Walter Chase, Auburndale, MA (US)

(73) Assignee: AMI Research & Development, LLC, Windham, NH (US)

( * ) Notice: Subject to any disclaimer, the term of this patent is extended or adjusted under 35 U.S.C. 154(b) by 0 days.

(21) Appl. No.: 14/466,026

(22) Filed: Aug. 22, 2014

(65) Prior Publication Data

US 2015/0054511 A1   Feb. 26, 2015

Related U.S. Application Data

(60) Provisional application No. 61/868,693, filed on Aug. 22, 2013, provisional application No. 61/868,658, filed on Aug. 22, 2013, provisional application No. 61/868,668, filed on Aug. 22, 2013, provisional application No. 61/979,081, filed on Apr. 14, 2014.

(51) Int. Cl.
*G01V 3/00* (2006.01)
*G01R 33/44* (2006.01)
(Continued)

(52) U.S. Cl.
CPC ............ *G01R 33/441* (2013.01); *G01N 24/084* (2013.01); *G01R 33/34046* (2013.01); *G01R 33/3621* (2013.01)

(58) Field of Classification Search
CPC ...................................................... G01R 33/441
USPC ......................................... 324/314, 316, 300
See application file for complete search history.

(56) References Cited

U.S. PATENT DOCUMENTS 5,457,385 A   10/1995   Sydney et al.
5,592,083 A   1/1997   Magnuson et al.
(Continued)

FOREIGN PATENT DOCUMENTS

JP   2009 264972 A   11/2009
WO   WO 99/45409 A1   9/1999
(Continued)

OTHER PUBLICATIONS

Peshkovsky A. S. et al. "Noise-resilient multi-frequency surface sensor for nuclear quadrupole resonance," Journal of Magnetic Resonance, Academic Press, Orlando, FL, vol. 194, No. 2, Oct. 1, 2008, pp. 222-229.
(Continued)

*Primary Examiner* — Louis Arana
(74) *Attorney, Agent, or Firm* — Cesari and McKenna, LLP

(57) ABSTRACT

A Nuclear Quadrupole Resonance detection system with features that include:
  a) slab radiating structure for the transmit path;
  b) reduced impedance transmit radiator;
  c) portal-embedded stripline couplers for receive path;
  d) wideband chirps each encompassing multiple simultaneous resonances;
  e) chirp sequencing enabling three channel architecture;
  f) magnetic amplification effect of ferrite-based directional couplers;
  g) determining position of substance within portal.

25 Claims, 41 Drawing Sheets

(51) Int. Cl.
*G01N 24/08* (2006.01)
*G01R 33/36* (2006.01)
*G01R 33/34* (2006.01)

(56) References Cited

U.S. PATENT DOCUMENTS

| | | | |
|---|---|---|---|
| 5,814,987 | A | 9/1998 | Smith et al. |
| 6,100,688 | A | 8/2000 | Smith et al. |
| 6,127,824 | A | 10/2000 | Smith et al. |
| 6,392,408 | B1 | 5/2002 | Barrall et al. |
| 7,365,536 | B2* | 4/2008 | Crowley et al. ............... 324/300 |
| 7,868,758 | B2 | 1/2011 | Barral et al. |
| 7,999,541 | B2 | 8/2011 | Chisholm et al. |
| 8,660,803 | B2* | 2/2014 | Apostolos et al. ............... 702/23 |
| 8,912,788 | B2* | 12/2014 | Apostolos et al. ............ 324/204 |
| 2006/0140249 | A1 | 6/2006 | Kohno |
| 2007/0018644 | A1 | 1/2007 | Flexman et al. |
| 2007/0096731 | A1 | 5/2007 | Peshkovsky et al. |
| 2014/0266209 | A1 | 9/2014 | Apostolos et al. |

FOREIGN PATENT DOCUMENTS

| | | |
|---|---|---|
| WO | WO 2004/003592 A1 | 1/2004 |
| WO | WO 2005/059582 A1 | 6/2005 |
| WO | WO 2011/094462 A1 | 8/2011 |
| WO | WO 2011/094463 A1 | 8/2011 |
| WO | WO 2011/094466 A1 | 8/2011 |
| WO | WO 2011/102948 A1 | 8/2011 |
| WO | WO 2011/126594 A2 | 10/2011 |
| WO | WO 2011/152887 A2 | 12/2011 |
| WO | WO 2013/049270 A1 | 4/2013 |
| WO | WO 2014/159803 A1 | 10/2014 |

OTHER PUBLICATIONS

International Search Report and Written Opinion, mail date Dec. 20, 2012 for International Application No. PCT/US2012/057425, International Filing Date Sep. 27, 2012, AMI Research & Development, Inc. 15 pages.

Itozaki et al. "Nuclear Quadrupole Resonance for Explosive Detection" Graduate School of Engineering Science, Osaka, 560-8531, Japan, International Journal on Smart Sensing and Intelligent Systems, vol. 1, No. 3, Sep. 2008, pp. 705-715.

International Search Report and Written Opinion mail date Jul. 30, 2014 for International Patent Application No. PCT/US2014/025196 filed on Mar. 13, 2014 by AMI Research & Development, LLC, 15 pages.

Gupta, R. K. et al., "Rapid scan Fourier transform NMR spectroscopy," Journal of Magnetic Resonance, Academic Press, London, GB, vol. 13, No. 3, Mar. 1, 1974, pp. 275-290.

Hyde, J.S. et al., "W-band frequency-swept EPR" Journal of Magnetic Resonance, Academic Press, Orlando, FL,US, vol. 205, No. 1, Jul. 1, 2010, pp. 93-101.

Apostolos, John T., et al., "Low-power stimulated emission nuclear quadrupole resonance detection system utilizing Rabi transitions," Proceedings of SPIE, SPIE-International Society for Optical Engineering, US, vol. 8709, Jun. 7, 2013, pp. 87090Q-1.

International Search Report and Written Opinion, mail date Feb. 18, 2015 for International Application No. PCT/US2014/066343, International Filing Date Nov. 19, 2014, AMI Research & Development, Inc. 17 pages.

\* cited by examiner

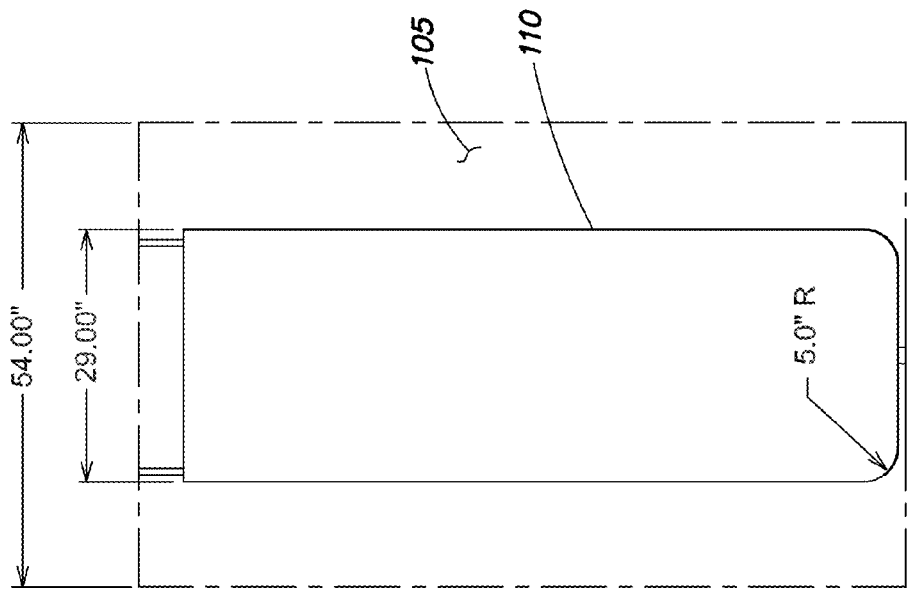
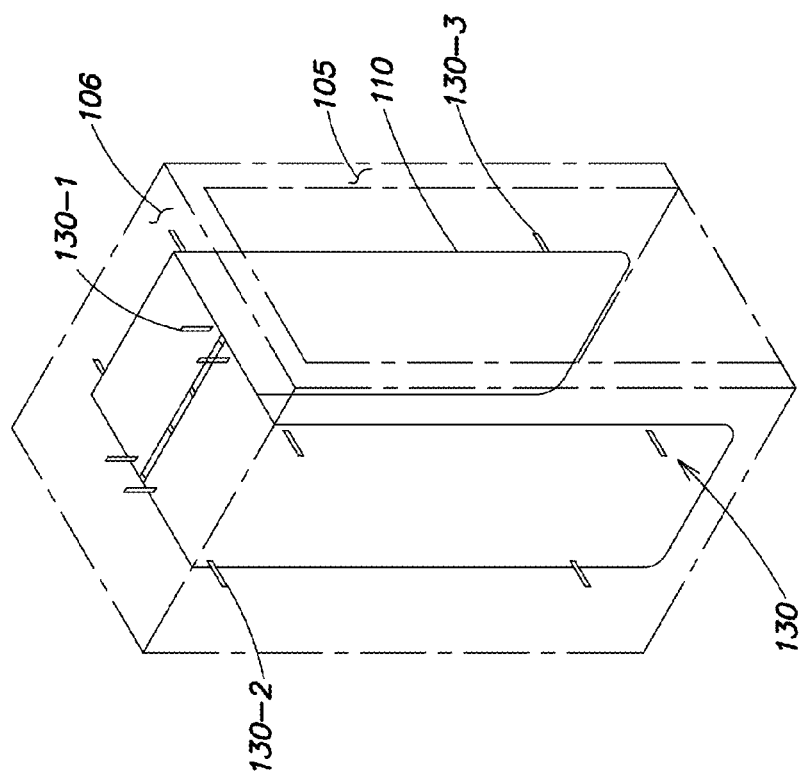

| Material | | Band 1 - kHz | Band 2 - kHz | Band 3 - kHz | Band 4 - kHz |
|---|---|---|---|---|---|
| 1 | RDX | 365-405 | 1765-1805 | 3390-3430 | 5005-5045 |
| 2 | PETN | 380-420 | 480-520 | 875-915 | |
| 3 | TNT | 100-140 | 730-770 | 830-870 | 930-970 |
| 4 | Ammonium Nitrate | 100-140 | 395-435 | 465-505 | |
| 5 | Urea Nitrate | 700-740 | 1980-2020 | 2700-2740 | |
| 6 | Glycine | 280-320 | 685-725 | 1030-1070 | |
| 7 | Sodium Nitrite | 1020-1060 | 3590-3630 | 4620-4660 | |
| 8 | HMX* | 1430-1470 | 1555-1595 | 3600-3640 | 3730-3770 |
| 9 | Potassium Nitrate* | 005-045 | 530-570 | 630-670 | |

FIG. 8B

Cal 1

| | | |
|---|---|---|
| GLY1 | 280 | 320 |
| UN1 | 700 | 740 |
| SN1 | 1020 | 1060 |

Cal 2

| | | |
|---|---|---|
| GLY2 | 685 | 725 |
| UN2 | 1980 | 2020 |
| SN2 | 3590 | 3630 |

Cal 3

| | | |
|---|---|---|
| GLY3 | 1030 | 1070 |
| UN3 | 2700 | 2740 |
| SN3 | 4620 | 4660 |

Run 1

| | | |
|---|---|---|
| RDX1 | 365 | 405 |
| TNT2 | 730 | 770 |
| PETN 3 | 875 | 915 |
| UN2 | 1980 | 2020 |
| HMX3 | 3600 | 3640 |

Run 2

| | | |
|---|---|---|
| AN2 | 395 | 435 |
| PETN 2 | 480 | 520 |
| UN1 | 700 | 740 |
| TNT3 | 830 | 870 |
| RDX2 | 1765 | 1805 |
| HMX1 | 1430 | 1470 |

Run 3

| | | |
|---|---|---|
| PETN 1 | 380 | 420 |
| AN3 | 465 | 505 |
| TNT4 | 930 | 970 |
| UN3 | 2700 | 2740 |
| RDX3 | 3390 | 3430 |
| HMX2 | 1555 | 1595 |

Waveform Run Sequencing

| | Frequenciew in kHz | | | | | |
|---|---|---|---|---|---|---|
| Amp # | Run 1 | Run 2 | Run 3 | Cal 1 | Cal 2 | Cal 3 |
| A1 | 385 | 415 | 400 | 300 | --- | --- |
| A2 | --- | 500 | 485 | --- | --- | --- |
| A3 | 750 | 720 | --- | 720 | 705 | 1050 |
| A4 | 895 | 850 | 1575 | 1040 | --- | --- |
| A5 | 2000 | 1785 | 2720 | --- | 2000 | 2720 |
| A6 | 3620 | --- | 3410 | --- | 3610 | 4640 |

Multiplexer Passbands

| Diplexer# | Min | Max | Min | Max |
|---|---|---|---|---|
| A1 | 270 | 440 | 270 | 550 |
| A2 | 460 | 530 | | |
| B1 | 670 | 785 | 650 | 1625 |
| B2 | 815 | 1615 | | |
| C1 | 1735 | 2770 | 1700 | 4700 |
| C2 | 3360 | 4690 | | |

FIG. 9B

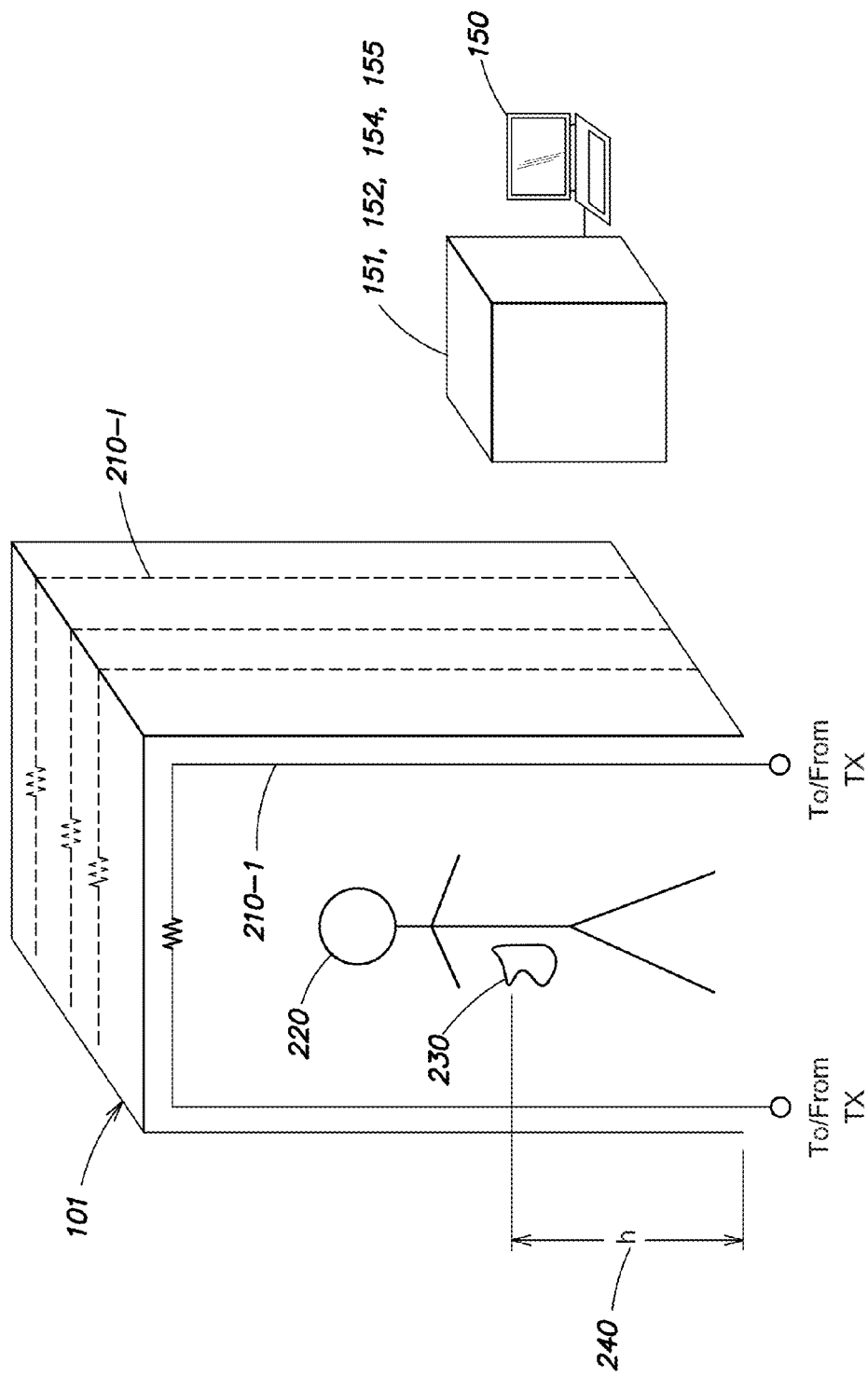

NUCLEAR QUADRUPOLE RESONANCE SYSTEM

CROSS REFERENCE TO RELATED APPLICATIONS

This application claims priority to several co-pending U.S. patent applications including Ser. No. 61/868,693 filed Aug. 22, 2013 entitled "Location of Materials on a Person Standing Within an NQR Portal"; Ser. No. 61/868,658 filed Aug. 22, 2013 entitled "Four Port Unified Coupler For NQR Portal"; Ser. No. 61/868,668 filed Aug. 22, 2013 entitled "Waveform Sequencing in Multiplexed NQR System"; and Ser. No. 61/979,081 filed Apr. 14, 2014 entitled "Three Channel System Architecture For Nuclear Quadrupole Resonance Detection And Other Features". The entire contents of each of these referenced co-pending patent applications are hereby incorporated by reference.

This application is also related to co-pending U.S. patent application Ser. No. 14/206,394 filed Mar. 12, 2014 entitled "Detection Processing for NQR System", the is entire contents of which is hereby incorporated by reference.

BACKGROUND

1. Technical Field

This application relates to chemical analysis and more particularly to systems and methods that use the Nuclear Quadrupole Resonance effect to determine the identity of a substance.

2. Background

As described in the above-referenced co-pending patent applications, a system that uses the Nuclear Quadrupole Resonance (NQR) effect for detecting a substance typically uses one or more conductive surfaces to define an area, or portal, that is to be monitored. Two or more conductors, typically thin wires, are disposed within the portal adjacent the conductive surfaces. The wires are each individually electrically terminated; alternatively, they can be arranged as balanced transmission lines. The wires are driven with a Radio Frequency (RF) transmitter that generates one or more continuously varying radio frequency modulated chirp signals. The wires then radiate electromagnetic energy into the portal.

The resulting time varying electromagnetic fields then stimulate Nuclear Quadrupole Resonance in any material with an electric quadrupole moment located within the portal to cause the material(s) to emit coherent Radio Frequency (RF) emissions. These coherent RF emissions are then detected and further processed to determine characteristics of the substance, such as by detecting their amplitude, phase and/or frequency.

SUMMARY

A system and/or method for detecting the presence of materials of interest by inducing Nuclear Quadrupole Resonance (NQR). A portal typically has at least three conductive surfaces including a pair of left and right opposing side walls and a roof disposed between the left and right side walls. A radio frequency chirp transmitter generates time varying signals to be emitted into the portal, and a radio frequency chirp receiver detects coherent emissions from materials disposed within the portal space that are responsive to the time varying signals.

In one specific arrangement, a transmit radiator structure is connected to the chirp transmitter. The transmit radiator includes a conductor running along and adjacent to the left side, roof, and right side of the portal. Also, a receive radiator structure is connected to the radio frequency chirp receiver. The receive radiator structure is physically separate from the transmit radiator structure.

The transmit radiator structure may be a slab radiator comprising a left, top, and right conductive slab surface, with each slab surface disposed adjacent a respective one of the left side, top, and right side of the portal. The conductive slab surfaces may have a width of more than ⅓ of a width of at least one side of the portal.

One or more capacitors may be disposed between a respective one of the left, top, or right slab surfaces and the left portal side, right portal side or roof to control the characteristics of the radiated field.

The transmit structure may optionally include a balun disposed between the left slab surface and right slab surface at one end thereof, and a resistor disposed between the left slab surface and right slab surface at an opposing end thereof.

The physically separate receive structure may include a resistive coupler such as a stripline conductor. The stripline conductor is disposed within the portal adjacent to and running inboard of at least one of the left or right side slab radiators. The stripline conductor may extend from a location near a bottom of the portal to a position near the roof. In this configuration, a terminating resistor may be connected to one end of the stripline conductor near the bottom of the portal and a coaxial cable connected to an opposite end of the stripline conductor. A second stripline conductor may be disposed adjacent another one of the left or right side slab radiators.

In another configuration, a directional coupler disposed between a transmit signal path and receive signal path provides magnetic field amplification.

In another implementation, a system and method for detection of materials via Nuclear Quadrupole Resonance (NQR) uses a portal formed of conductive surfaces including at least a pair of left and right opposing side walls and a roof disposed between the left and right side walls. At least one conductor is disposed within the space adjacent the conductive surface. A radio frequency chirp transmitter emits a time varying electromagnetic field into the portal to induce NQR in the materials of interest. A coupler couples the radio frequency chirp transmitter to the conductor. If the transmit and receive structure are an integrated radiator, a directional coupler may be used to separate the transmitter and receiver signals. The directional coupler may be a four port directional coupler including a series inductive and/or parallel capacitive coupling between an input port and an output port, a first resistive coupling between the input port and a reference port, and a second resistive coupling between the output port and a signal port.

In another aspect, a processor controls the radio frequency chirp transmitter to generate multiple simultaneous chirp signals, but further constrained such that only one of the multiple NQR resonance frequencies of interest for a specific material is generated at a given time. In a specific arrangement therein, the transmitter may include three channels with bandwidths that range for example, from 360 to 940 kHz, 1370 to 2030 khz, and 3300 to 3830 khz.

In still other optional configurations, the multiple simultaneous chirp signals may be generated using three diplexers, each coupled to a selected pair of digital-to-analog converters (DACs), and each diplexer having a pair of bandpass filters. In this configuration, a triplexer is coupled to the three diplexers to provide a combined broadband chirp signal to the portal.

In another configuration, a first diplexer comprises bandpass filters having passbands from 270 to 440 khz and from 460 to 530 khz; a second diplexer uses bandpass filters having passbands from 670 to 785 khz and from 815 to 1615 khz; and a third diplexer includes bandpass filters having passbands from 1735 to 2770 khz and from 3360 to 4690 khz. Here, a triplexer includes a first bandpass filter having a passband from 270 to 550 khz; a second bandpass filter having a passband form 650 to 1625 khz; and a third bandpass filter having a passband from 1700 to 4700 khz.

In yet another configuration, the processor further processes detected NQR signals and a reference signal to determine a relative position of the substance within the portal. For example, a relative phase difference between the detected NQR signals and the reference signal indicates a relative height of the substance within the portal.

If multiple conductors are disposed within the portal, such that at least two opposing left and right conductive surfaces have at least one adjacent conductor, the processor may determine a relative signal strength between NQR response signals received on the two conductors to further determine a relative left and right side position of the substance.

Furthermore, if multiple conductors are disposed along at least one of either the left or right side surfaces, the processor can compare a relative signal strength between NQR signals received from the plurality of conductors to determines a relative depth of the substance within the portal.

Another configuration uses a conductive wire having one end coupled to at least one of the chirp transmitter and/or receiver, and another end coupled to a terminating resistor, the conductive wire running along and adjacent to the left side, roof, and right side of the portal. In this embodiment, a plurality of conductive wires may be run along and adjacent to the left side, roof, and right side of the portal, each coupled to a respective terminating resistor.

BRIEF DESCRIPTION OF THE DRAWINGS

The description below refers to the accompanying drawings, of which:

FIGS. 2A-2H illustrate certain aspects of a slab radiator used in a transmit path.

FIG. 8B is a chart of chirp signals used to detect the various materials of interest.

FIGS. 9A and 9B show both (a) sequencing of chirp waveforms such that only one chirp per material of interest is generated at any given time, but such that a multiplexed transmitter generates up to six chirps in parallel and (b) passbands for a six to three channel RF multiplexer.

FIG. 13 is a schematic view showing the location of the wire loops within the portal and a person carrying a substance of interest at a height, h, above the floor.

DETAILED DESCRIPTION OF PREFERRED EMBODIMENTS

1. System Overview

Figure 1:
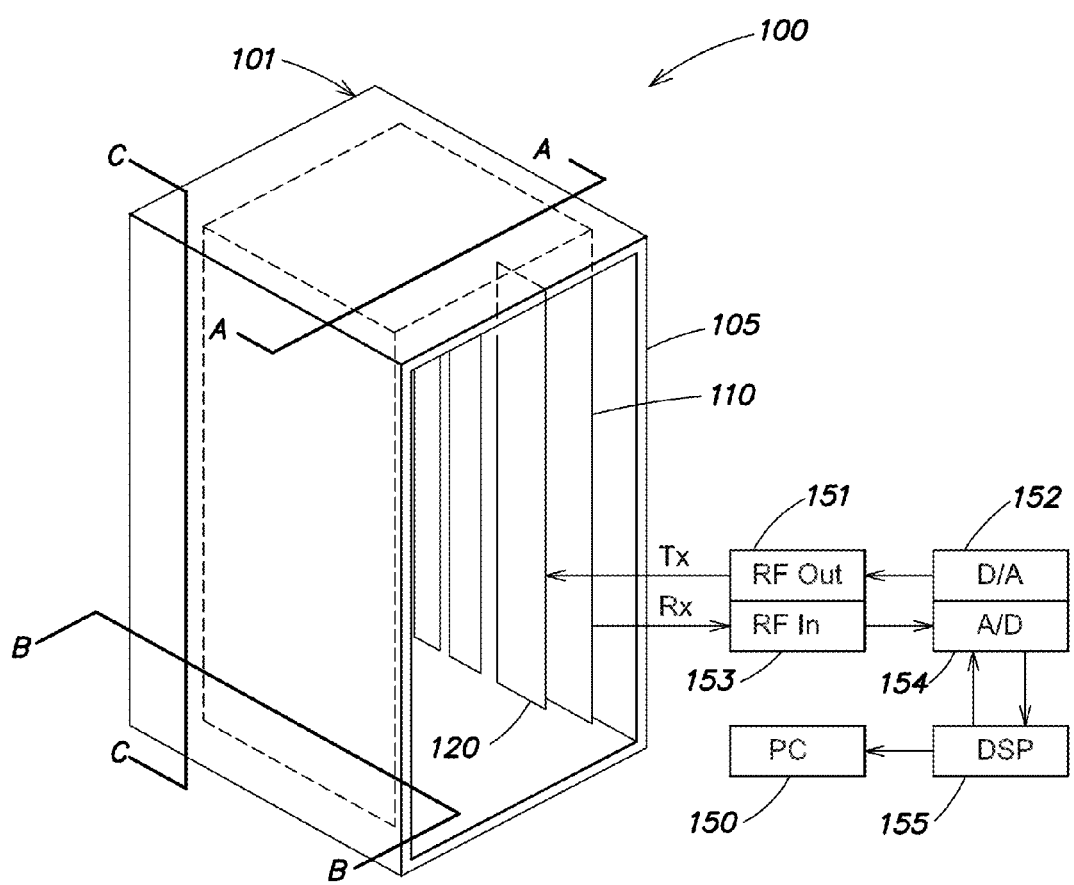
FIG. 1 is an isometric view of a portal using slab radiators and, separate stripline couplers.

FIG. 1 is a high-level diagram of the components of a Nuclear Quadrupole Resonance (NQR)—based material detection system 100 according to one embodiment of the teachings herein. In general, the NQR system may include a portal 101 into which materials of interest are placed.

A programmable data processor such as a personal computer (PC) 150 controls digital circuits and/or processors and analog circuits (such as transmitter 151 (RFout) and D/A converters 152) that generate radio frequency (RF) signals. The transmitter RF signals (Tx) are coupled to transmission line(s) or other conductors, or conductive surfaces disposed within the portal walls to cause electromagnetic fields to be generated within the portal 101. Receiver circuitry 153 (RFin) detects a receive signal (Rx) that includes an NQR response of a material disposed within the portal. The system then digitizes the response signals with one or more A/D converters 154 and forwards the detected response to the PC and/or a Digital Signal Processor (DSP) 155 for further processing. The DSP 155 and/or PC then make a decision as to whether there are certain types of materials in the portal, and displays the result.

Although specific configuration details will vary, the personal computer (PC) 150 may have the typical central processing unit (CPU), memory, disk and/or other mass storage devices, and a display (not shown). The PC stores and executes software programs that implement the functions described herein. A power supply (not shown) provides power to the PC as well as to the other components of the system. An input/output (I/O) subsystem (also not shown), which may be a peripheral board plugged into the PC via an suitable interface includes transceiver circuits and a number of digital to analog converters and analog to digital converters.

In addition, the PC may include a subsystem that houses one or more Digital Signal Processor (DSP) 155 hardware chips and/or software platforms to implement transmit signal generation and receive signal detection functions.

More particularly, in the transmit direction, the PC 150 controls the DSP(s) 155 and/or D/As 152 to generate desired chirp signals that include one or more NQR frequencies of interest. More particularly, each of many RF signals may include a linear chirp signal, for example, a sinusoidal signal having an instantaneous frequency that changes linearly with time. The instantaneous frequency of each chirp signal may be mathematically represented as $$\omega_{instantaneous} = 2\pi F_{start} + 2\pi\left(\frac{BW}{T}\right)t$$

where $F_{start}$ is an initial frequency, BW is a bandwidth (frequency range in hertz) of the chirp, and T is the duration of the chirp.

The chirp signals preferably originate as digital signal data computed and/or stored by the PC and/or DSP. Each digital chirp signal, associated with one or more NQR frequencies of interest, is fed to one of the D/As, is low-passed filtered, and amplified. Multiple analog chirp waveforms with alternating power state illuminations may be generated at a given instant in time via the D/As, filters, and amplifiers operating in parallel in the Radio Frequency output (RFout) circuits 151.

The magnetic field(s) generated in response to the transmitted chirp signals are then made incident on whatever is contained in the portal 101, causing coherent NQR emissions from certain types of materials. The response signal(s) from the portal contain the transmitted energy, reflected energy, and the NQR chirp signal(s).

Signals returned from the portal are fed to corresponding RF input (RFin) circuits 153 and A/D converters 154 to provide digital response signals back to the DSP 155 and/or PC 150 for receive signal processing. The receiver processing may include down conversion, demodulation (de-chirping), matched filtering, and other detection processing.

In one example, the receiver and detection processing described in U.S. patent application Ser. No. 14/206,394 filed Mar. 12, 2014 incorporated by reference may be used. More details of the signal generation, detection and processing, as well as alternative system architectures and components are described below and are also described in the patent applications that were incorporated by reference above.

More details of the quadrupole resonant frequencies of interest, and thus the preferred frequency ranges of the transmitted chirp signals needed to detect certain is materials are provided below.

2. Slab Radiator for Transmit

Of interest in FIG. 1 is the use of one or more slab radiator structures 110 for emitting transmitter signals (Tx) into the portal 101, as well as one or more stripline type couplers 120 for receive signal (Rx) detection. The slab structure(s) 110 are typically disposed within the portal adjacent both a portal left and right wall 105 and portal top surface that act as an RF shield. The stripline couplers 120 are located in-board of, separate from, spaced apart from the slab structure(s) 110.

FIG. 2A is a more detailed isometric view of one embodiment of portal 101 showing a single slab type transmit radiator 110 in more detail (please note the stripline couplers 120 are not seen in this view). FIG. 2B is a left side view. Slab radiator 110 generally consists of several relatively wide pieces of conductive material such as aluminum. The slab pieces are disposed inside the portal, adjacent each of the left and right sides of the portal as well as adjacent the portal roof 106. In the illustrated embodiment, the width of the conductive pieces is approximately 29 inches, preferably somewhat more than one-half the 54 inch depth of the portal walls, and at least the depth of the portal walls.

Given their relative wide surface area, the slab radiators thus operate as a form of microstrip radiator.

Although FIG. 2A shows an embodiment with a single wide slab (including the connected left side, top, and right side slab pieces), it should be understood multiple slabs may be disposed adjacent the portal walls in other embodiments.

As shown, a number of capacitors 130 may be connected in shunt configuration between each respective slab section and the metal portal sides 105 and/or roof 106. Capacitances 130-1 connected to the roof portion 106 may be about 360 pF, upper capacitances 130-2 may be about 1750 pF, and capacitances 130-3 near the bottom about 2100 pF. Addition of these shunt capacitors provides some series inductance. The capacitor values should be adjusted depending on the particular frequencies of interest and the exact portal and slab dimensions. More particularly, the shunt capacitors are selected to effectively cancel reactance and thus assist with eliminating the need for transceiver impedance matching networks if possible.

Providing a single wide conductor to form the radiating structure, as opposed to multiple wires or wire loops as in prior embodiments provides improved impedance and reduces discontinuities in the generated magnetic field.

The capacitors 130 and slab material are also designed to provide an effective impedance of approximately 12.5 ohms. This further increases the strength of the radiated magnetic field by about 6.0 dB. As a result, any associated balun or other transmitter circuitry (not shown in FIG. 2B) should also have a characteristic impedance reduction of the transmitter output, e.g. 50 ohms to 12.5 ohms.

In a case where the sides of the portal are 54 inches wide and the slab pieces may be 29 inches wide, a 5 inch radius rounding fillet may be placed around the bottom corners of the side slab pieces.

Figure 2C:
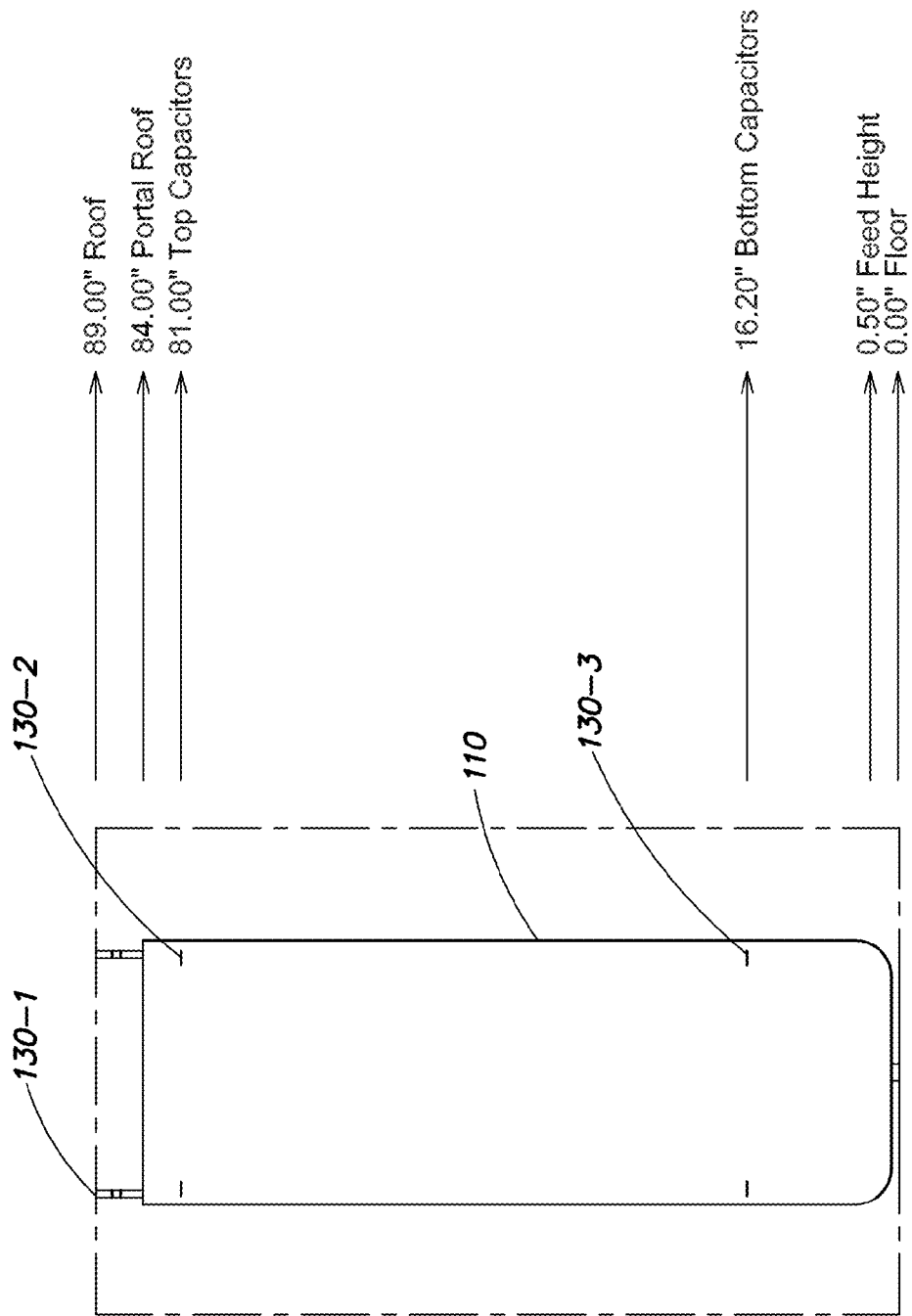

FIG. 2C also shows some additional dimensions illustrating the relative spacing along the height dimension. For example, the slab feed 110 begins at approximately ½ an inch from the portal floor, and extends upward to approximately 5 inches from the roof. The bottom capacitors 130-3 are placed 16.2 inches from the bottom and the top capacitors 130-2 approximately 81 inches from the bottom.

Figure 2D:
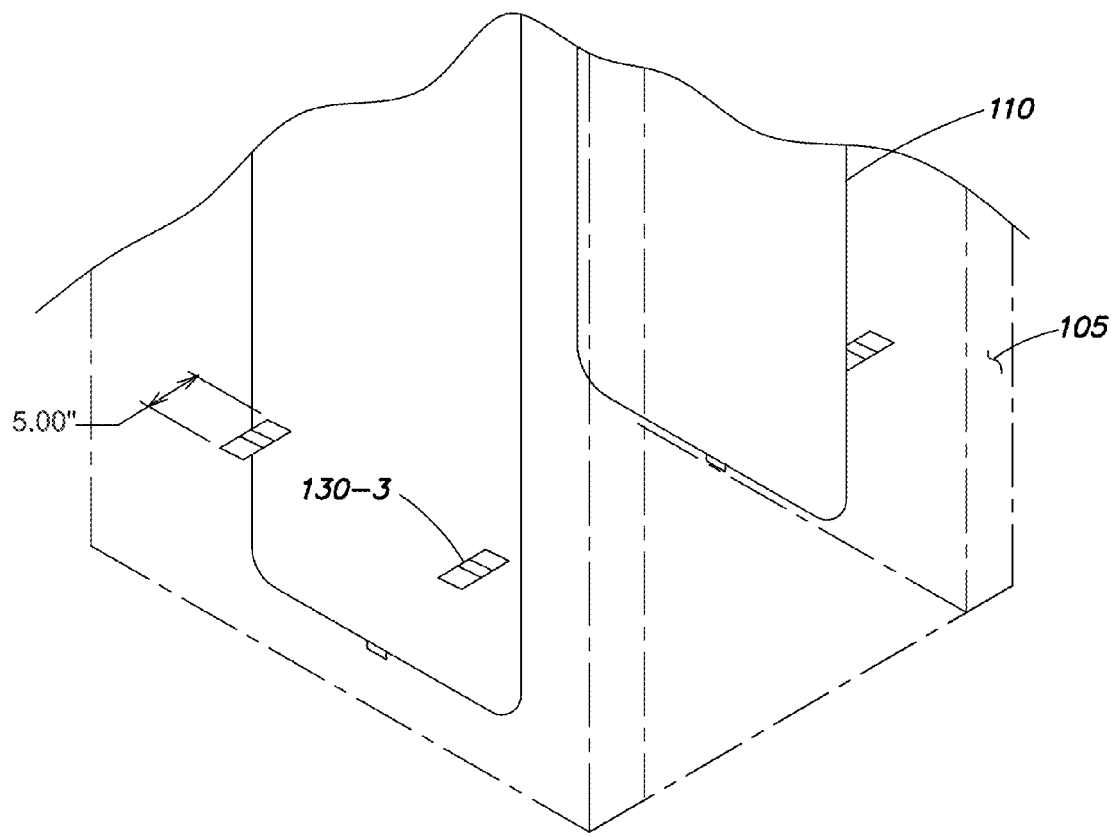
Figure 2E:
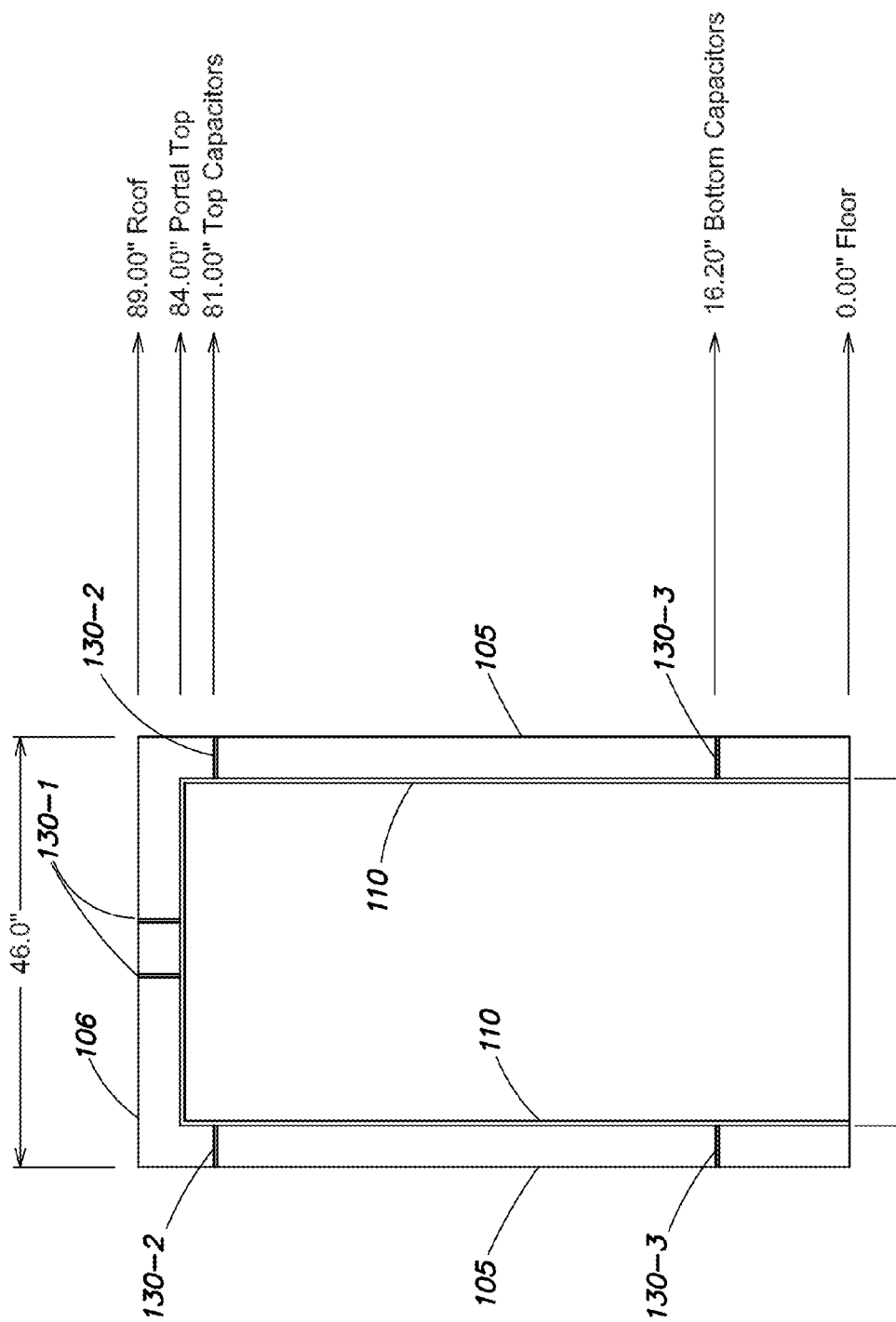
Figure 2F:
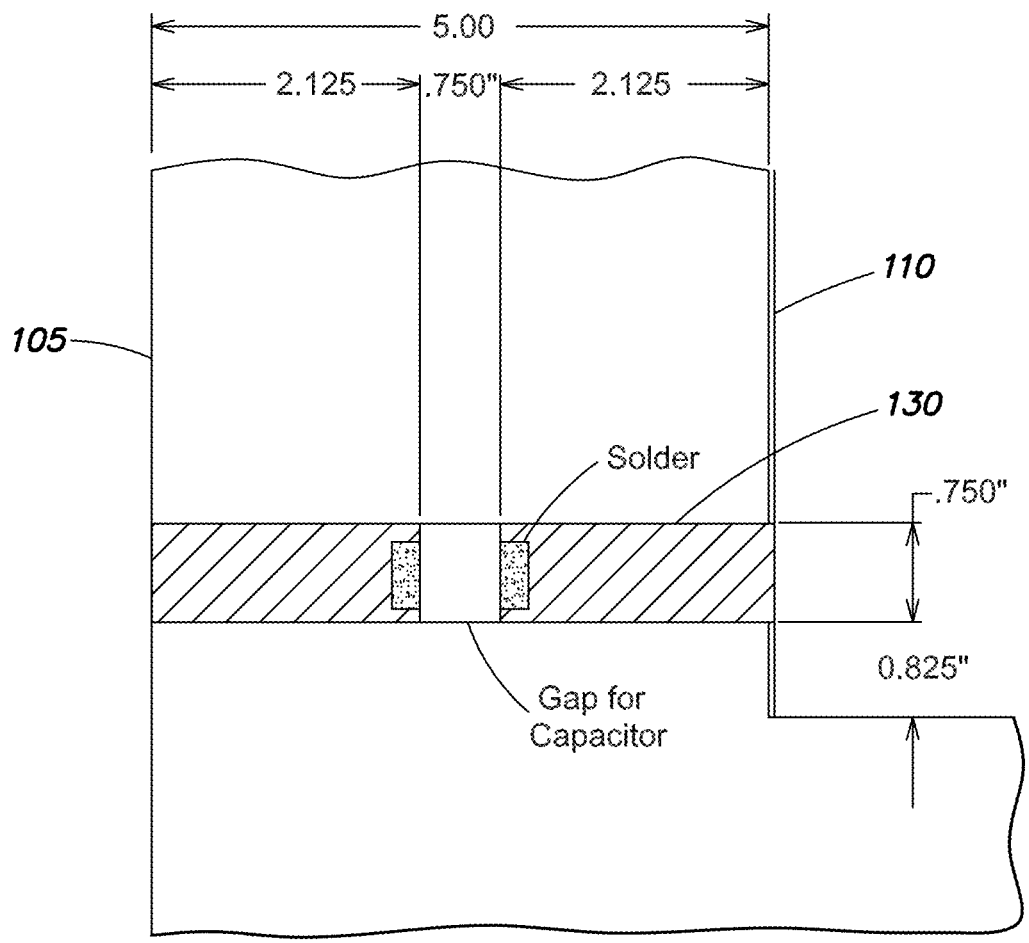

FIGS. 2D, 2E and 2F shows the slab and the interior surface of the portal, with the location of the bottom capacitors 130-3 in more detail. The spacing between the portal walls and roof and slab pieces is maintained at 5 inches all around.

As best shown in FIG. 2F, the capacitors may each be disposed in approximately the middle of an elongated, 5 inch long substrate such as a printed circuit board. Aluminum conductors on the printed circuit board substrate provide connections to the slab and portal wall.

Figure 2G:
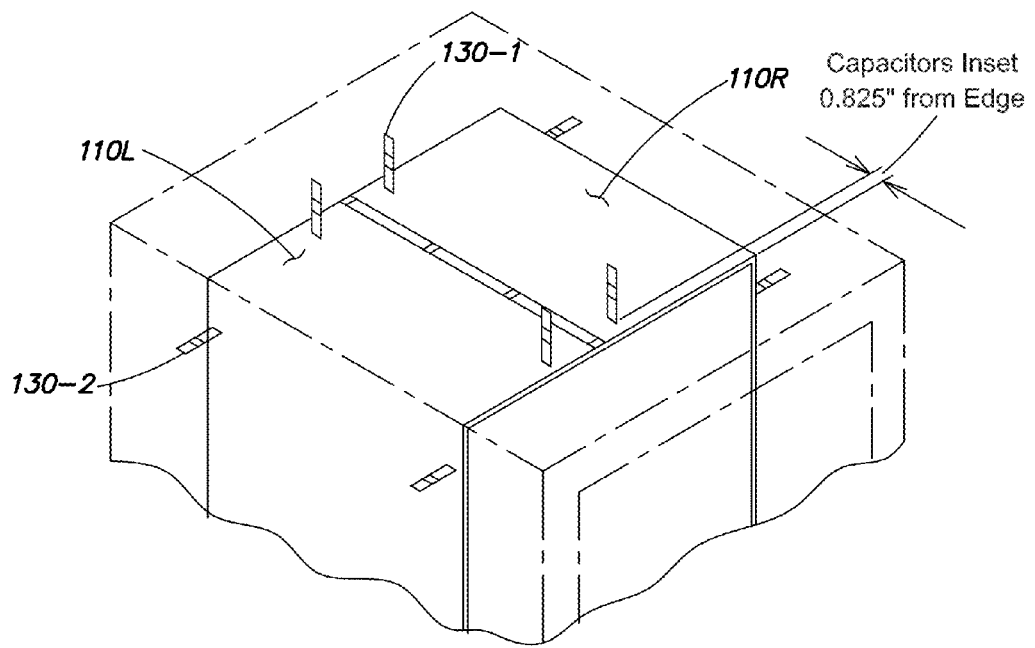
Figure 2H:
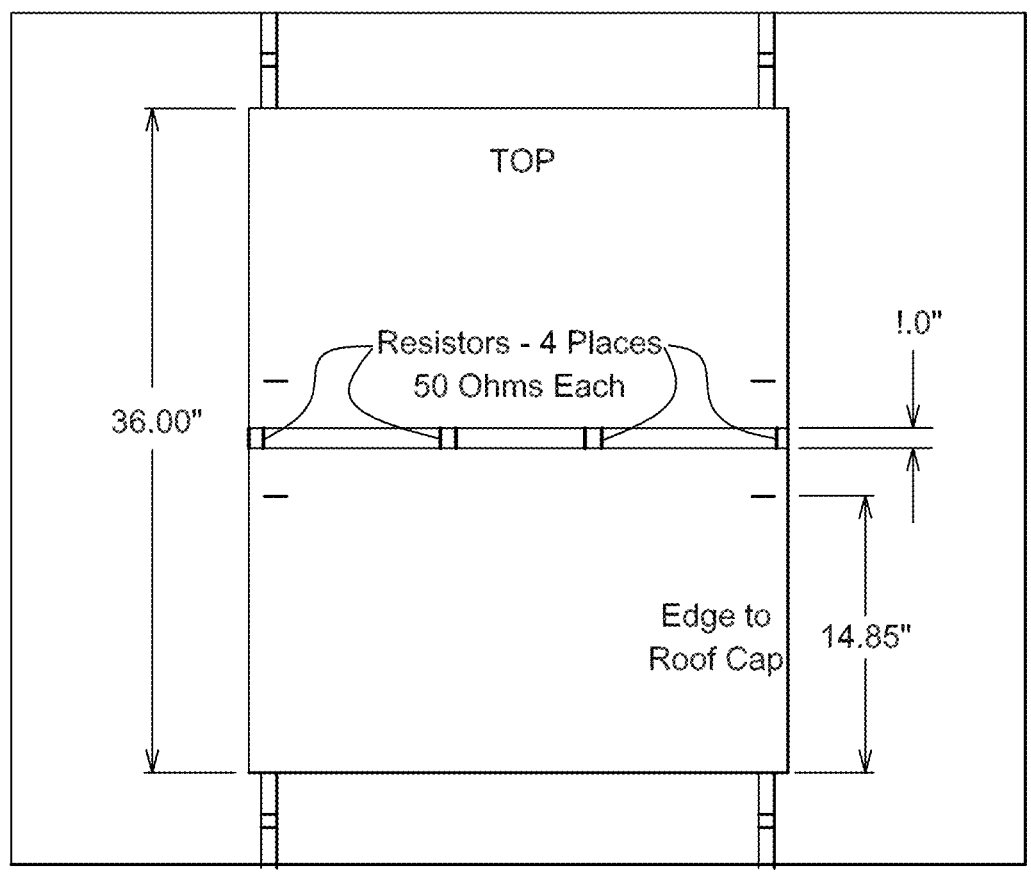

FIGS. 2G and 2H show more detail of the roof portion. The roof capacitors may be inset 0.825 inches from the edge of the slab. FIG. 2G also shows the slab radiator is actually formed from a left half 110-L and right half 110-R slab radiator portion, with a set of resistors such as 4 resistors connected in parallel, connecting the two half slabs near the roof. The gap between the two slabs sections 110-L, 110-R may be for example 1 inch. These dimensions are for a slab provided with a 36 inch depth.

FIG. 2E is a front view of the portal, indicating for example, that the distance between the portal top, sides and slab section may be 5 inches all around. The portal opening size, that is, the space between the left and right interior surfaces is 36 inches. The portal may have a maximum width dimension of 46 inches—that is, between the outermost surfaces of the shield.

Figure 3A:
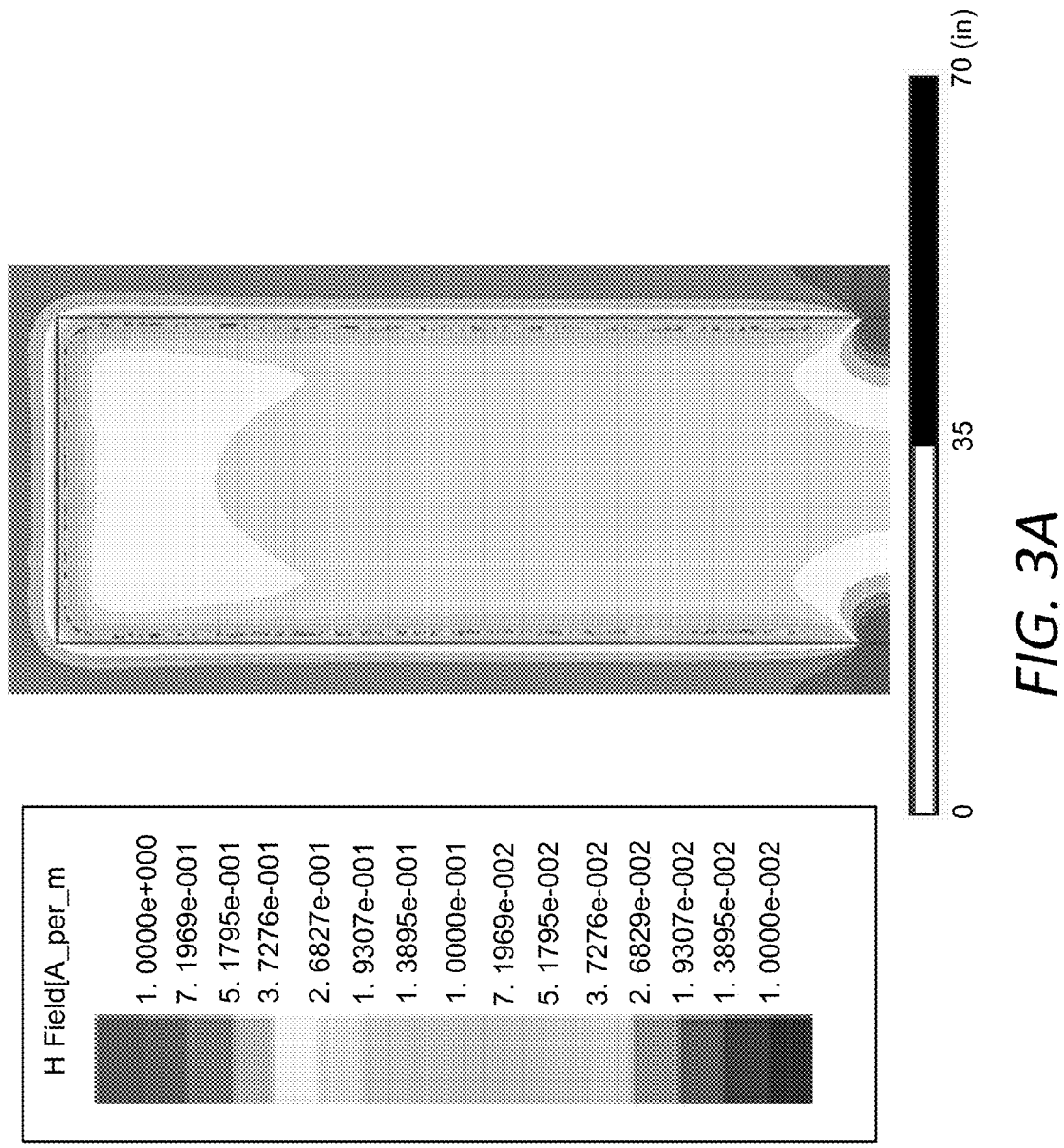
FIGS. 3A-3F show improvement in radiated field patterns with the FIG. 2A-2H configuration.
Figure 3B:
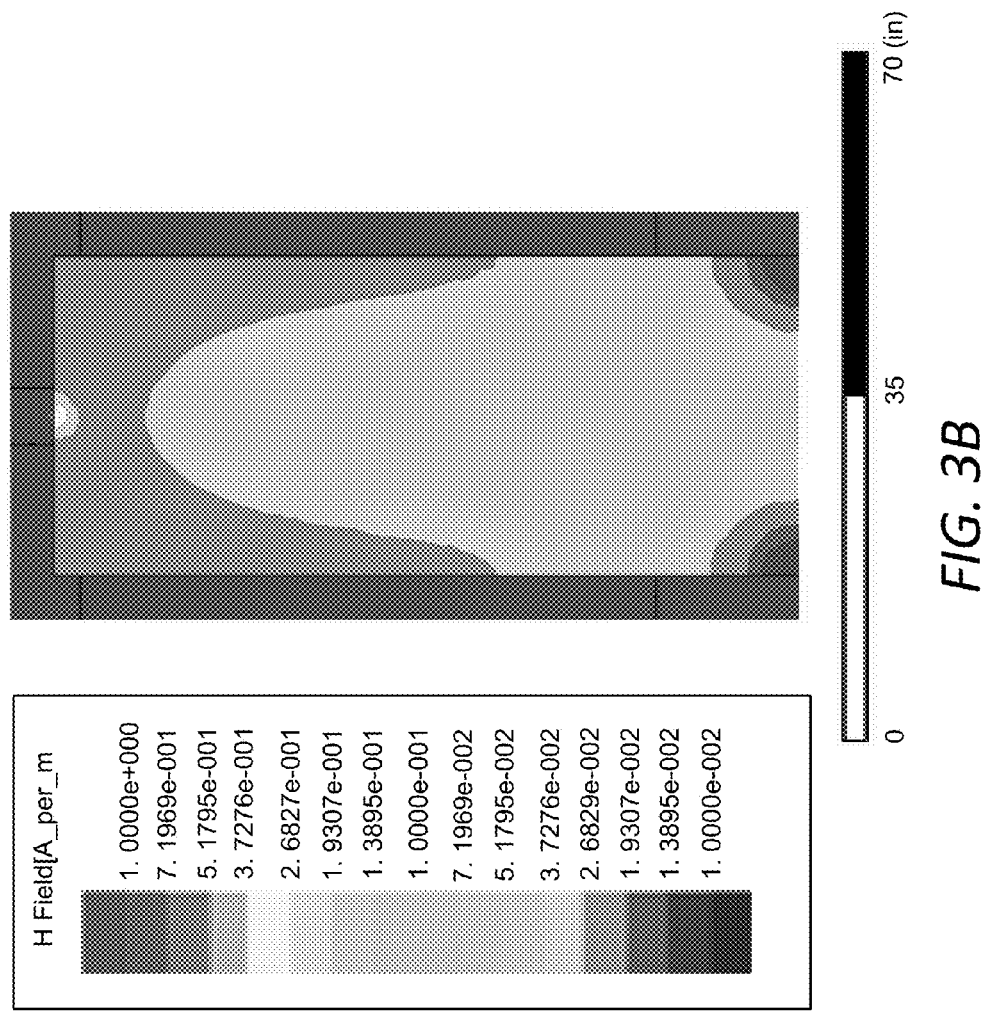

Comparison of FIGS. 3A and 3B shows the relative improvement provided by the use of the slab radiator 110. FIG. 3A is a simulated measurement showing the magnetic field strength achievable with a prior art design making use of a set of thin wires as the radiators. FIG. 3B is the same measurement taken with the slab radiator shown in FIGS. 2A-2H, thus showing the improvement.

Figure 3C:
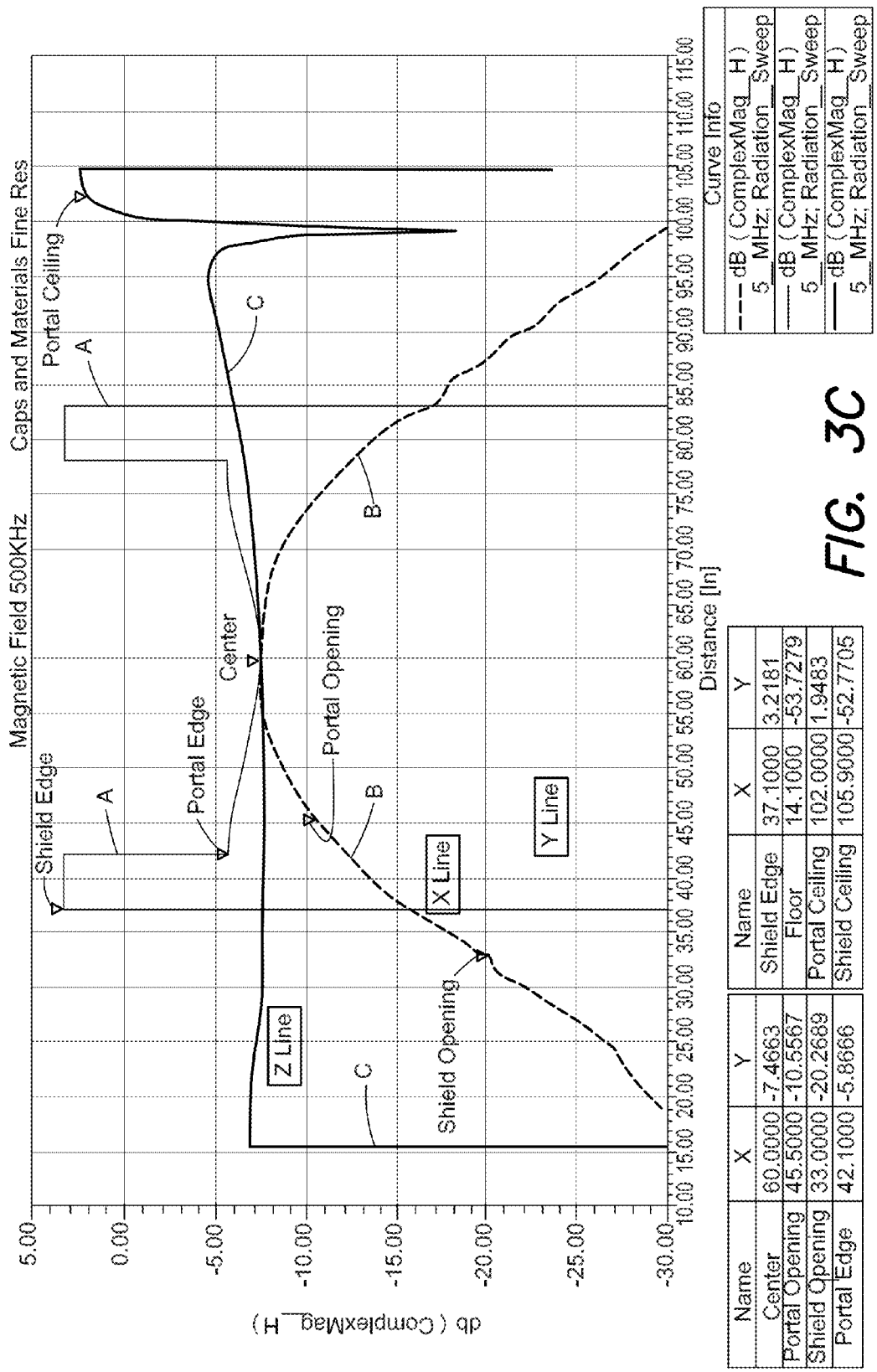

FIGS. 3C, 3D, 3E and 3F further show the resulting relative uniformity of magnetic and electric fields in three dimensional space. For example FIG. 3C shows the relative strength of the magnetic fields at 500 kHz along three planes of interest in the portal. The first curve A shows the simulated magnetic field strength looking inward at the portal, that is along plane A-A of FIG. 1. The left and right shield edges and corresponding left and right portal edges are distinctly shown. Fields at the center of the portal are relatively uniform from left to right. Curve B shows relative field strength in the plane defined by line B-B in FIG. 1. This is a front to back magnetic field strength plot, the portal opening and Portal center are shown. Finally, curve C shows the floor-to-ceiling profile, that is on the plane defined by line C-C in FIG. 1. The field strength is seen to be relatively uniform until a location approaching approximately 10 inches below the portal ceiling.

Figure 3D:
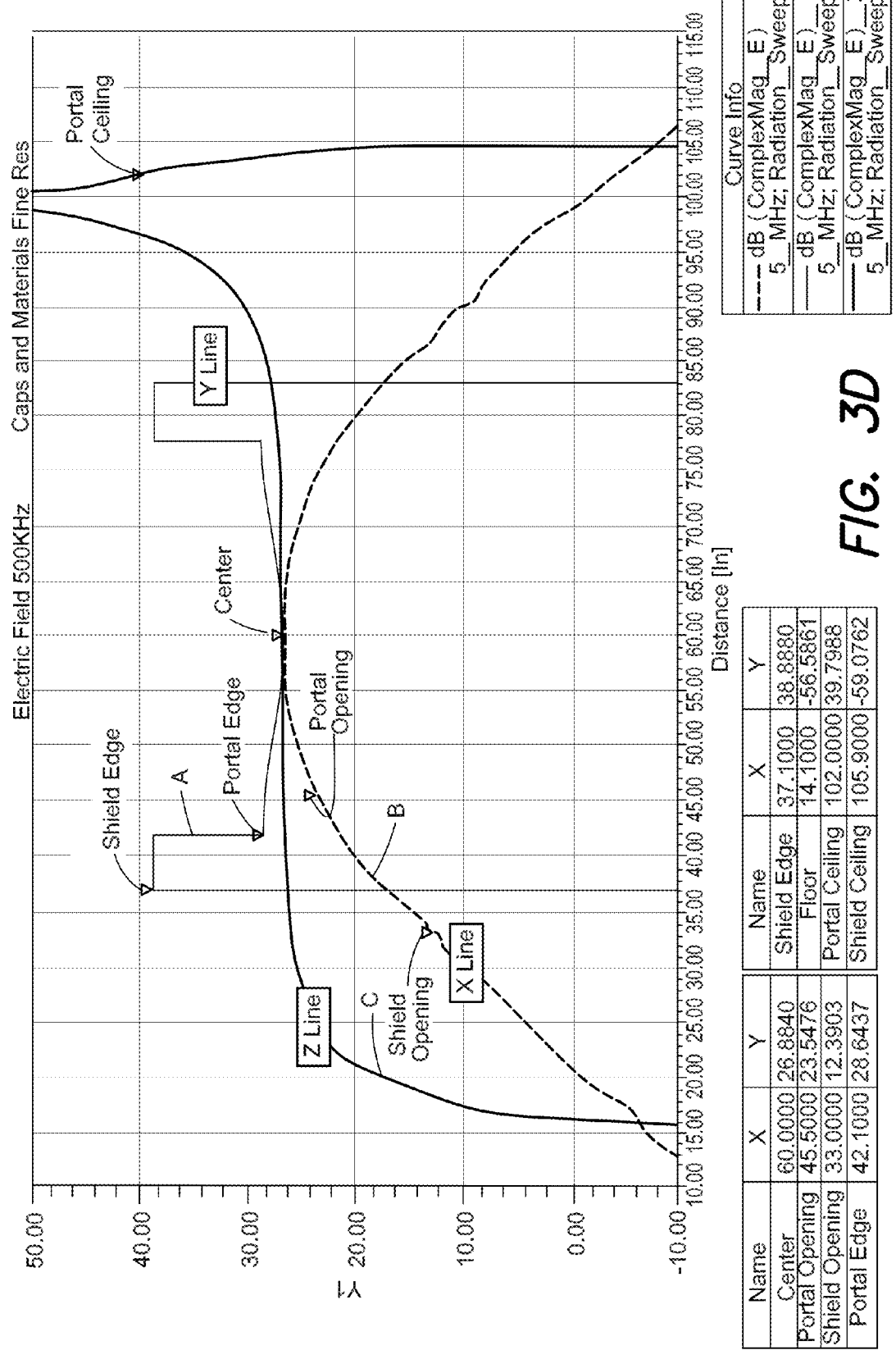
Figure 3E:
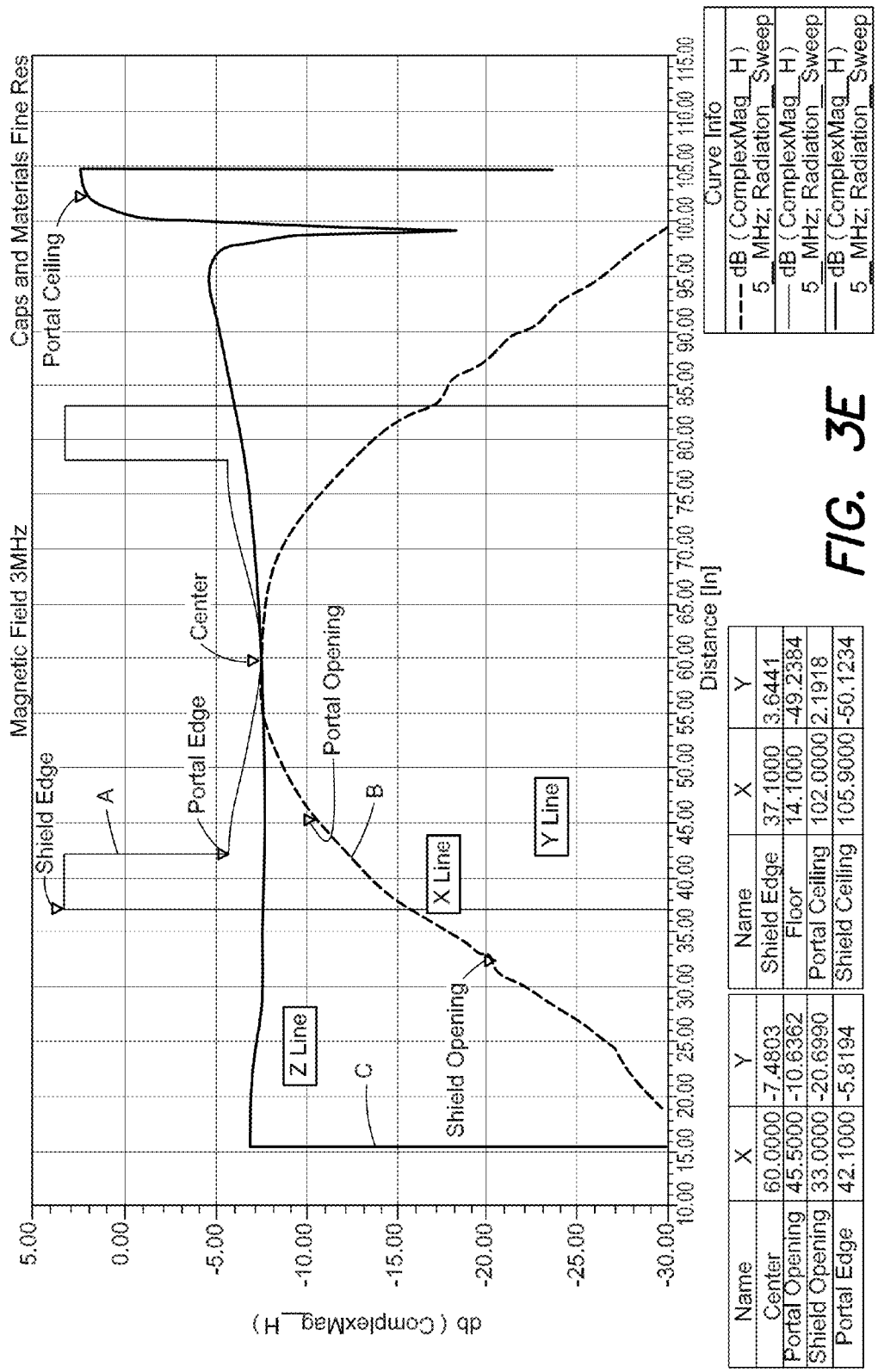
Figure 3F:
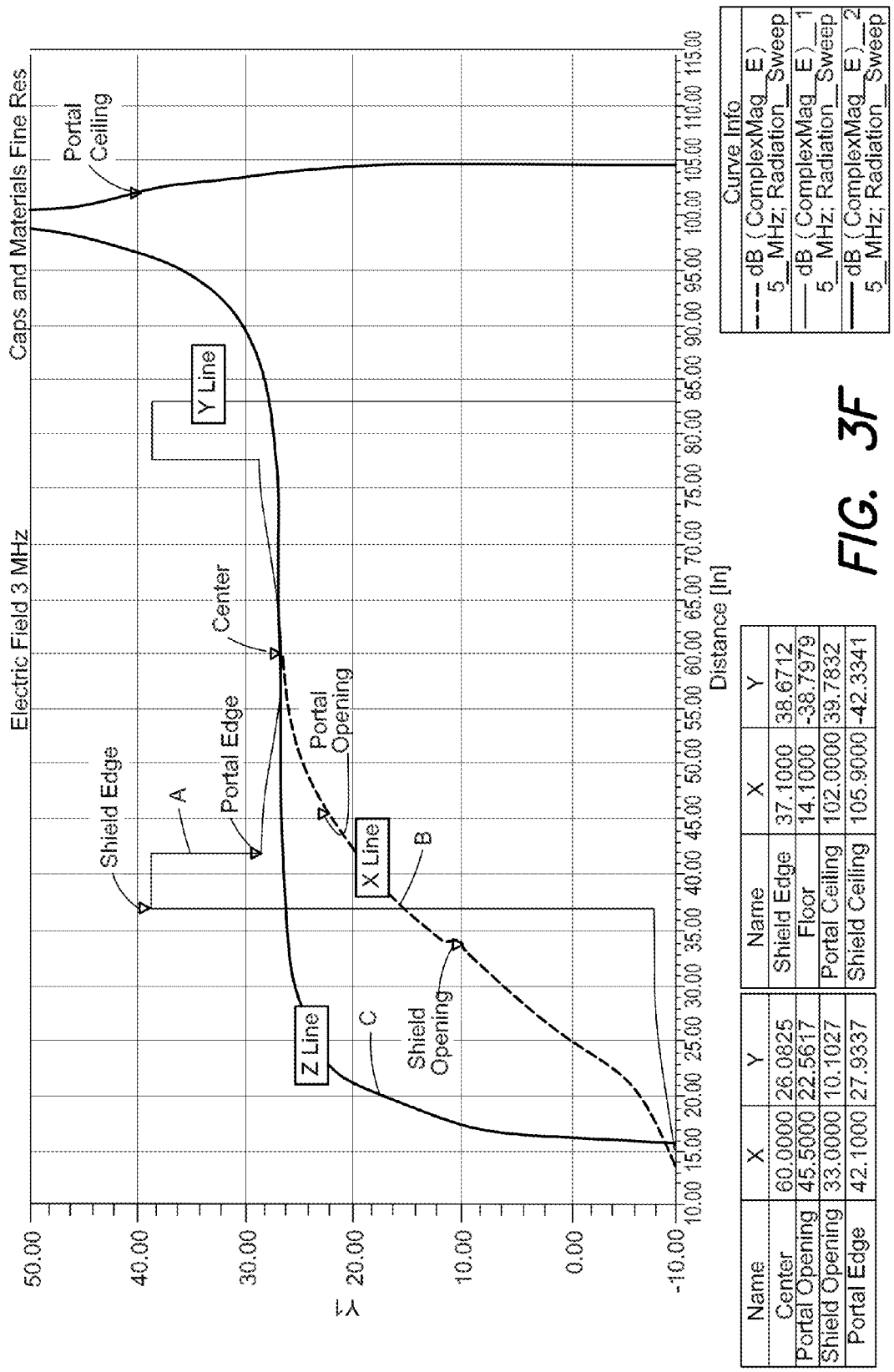

FIGS. 3D, 3E and 3F are similar plots of electric field at 500 kHz, magnetic field at 3 MHz, and electric field at 3 MHz.

These plots also exhibit relatively uniform field strength across the portal for frequency ranges of interest using the slab type radiators.

3. Separate Stripline Couplers for Receive

Figure 4A:
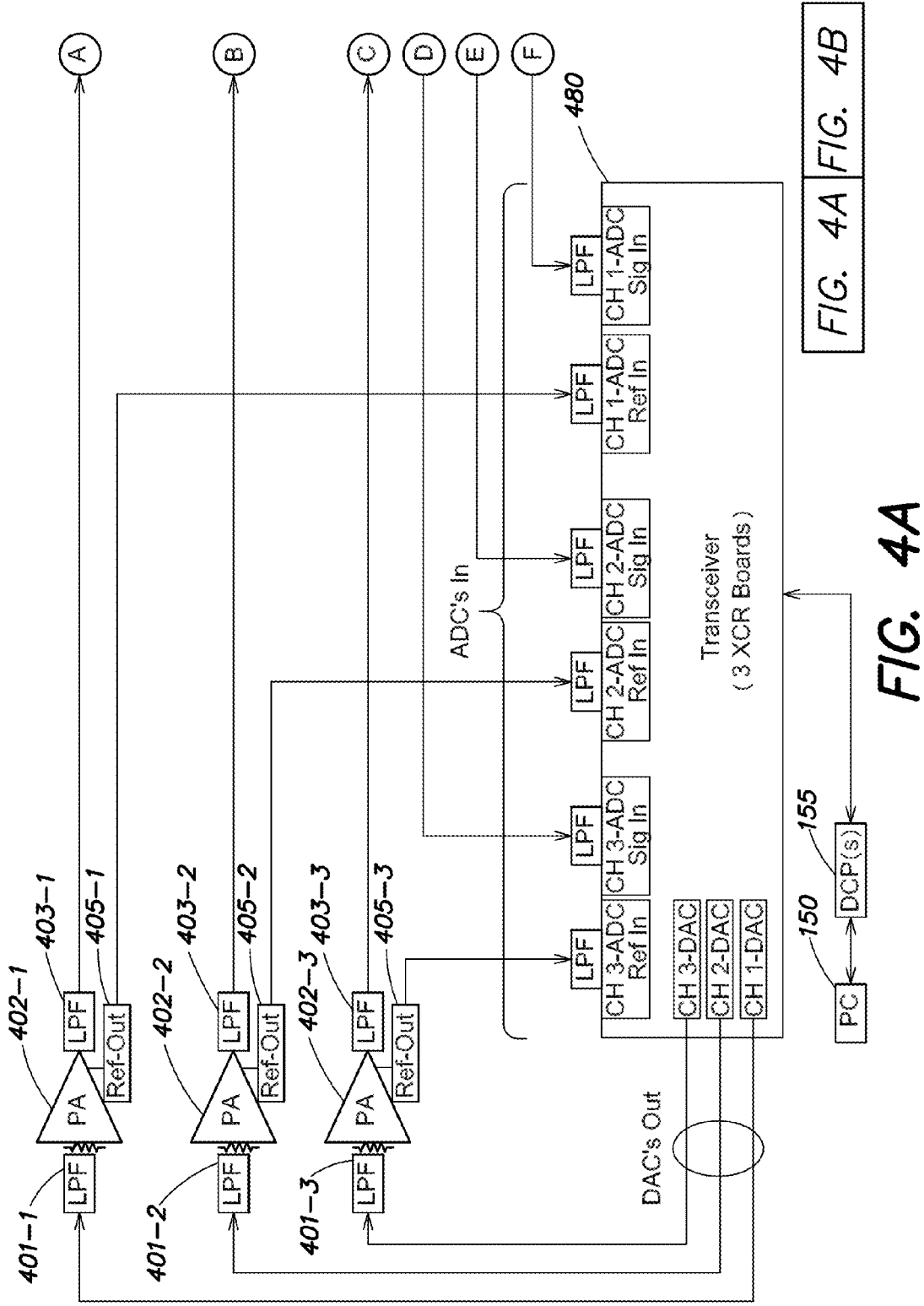
FIGS. 4A-4E are various configurations for embedded stripline couplers used in a receive path.
Figure 4B:
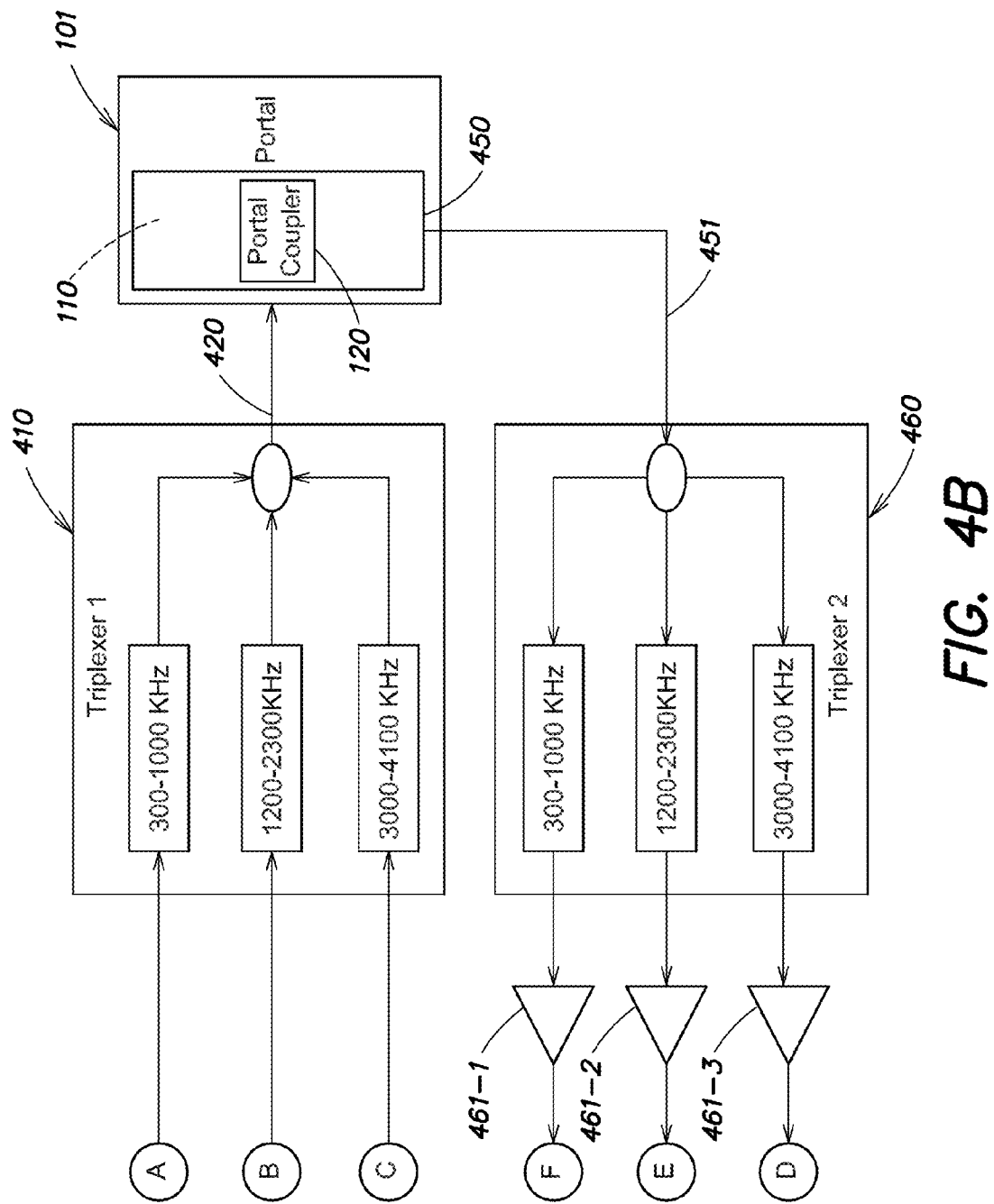
Figure 4C:
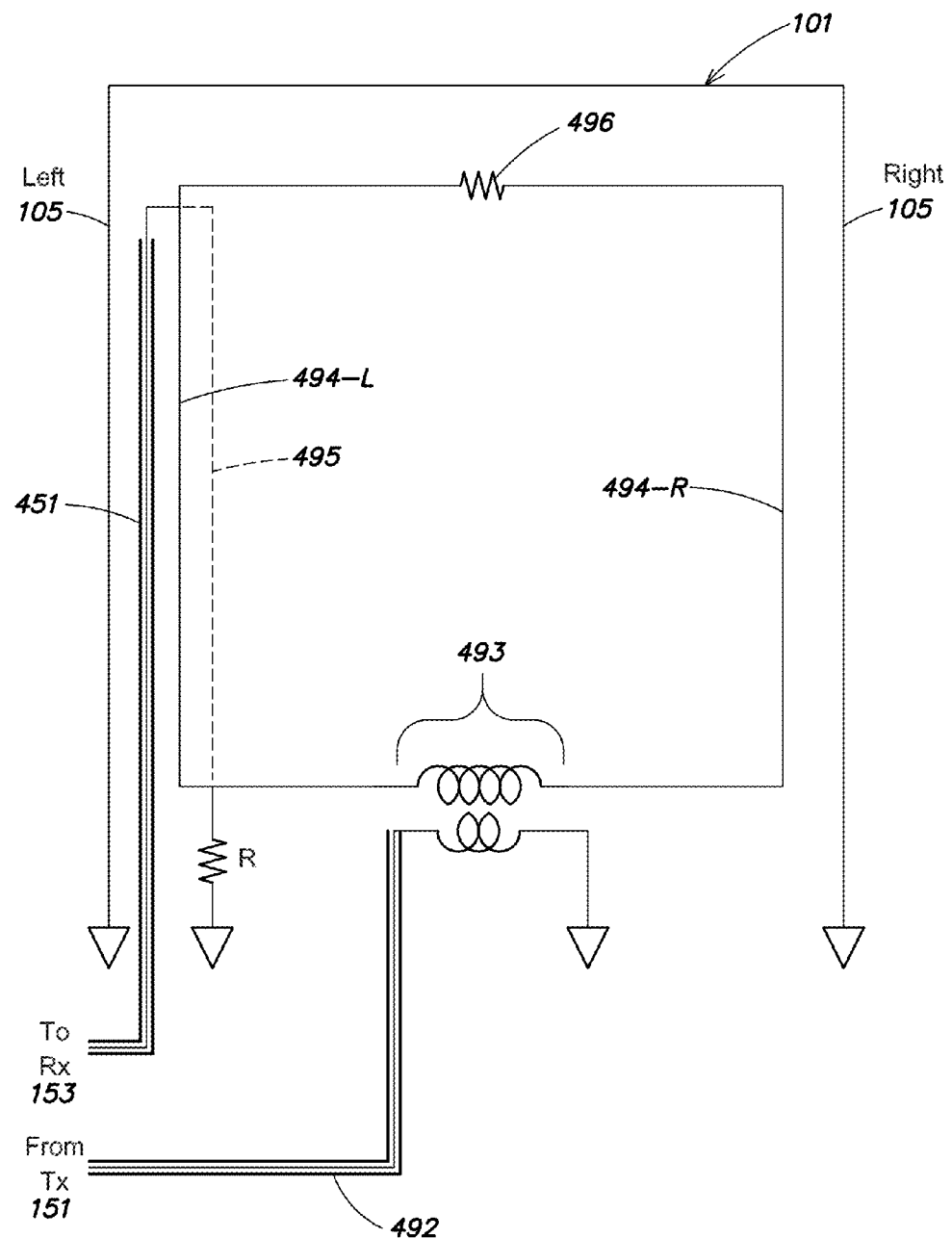

As shown in FIG. 1 the portal 101 may also include separate coupling structures 120 for receiving NQR signals emitted from materials located in the portal. One implementation of the radio frequency components for the transmitter and receiver (transceiver) in this configuration is shown in FIGS. 4A and 4B. As will be described in more detail below, this particular implementation is a "three channel" implementation where selected ones of the NQR frequencies of interest are grouped and processed in three frequency bands using broadband chirps. In this configuration, the transmit circuitry may include three channels with each channel including a first low pass filter 401-1, 401-2, 401-3 a power amplifier 402-1, 402-2, 402-3 and second low pass filter 403-1, 403-2, 403-3. The outputs of second low pass filters 403-1, 403-2, 403-3 are then fed to respect respective inputs of a transmit triplexer 410 which contains suitable bandpass filters before feeding the portal. Typical filer passbands are discussed in more detail below.

The transmit triplexer output signal 420 may for example be provided to the slab radiator as described above. However, in other embodiments the set of conductive wire loops as described in more detail below and the other patent applications referenced above may also be used as the radiators.

On the receive side one or more portal couplers 450 (in this implementation a single stripline coupler 450 corresponding to stripline coupler 120 of FIG. 1) provides a receive signal path 451 to a receive triplexer 460 which filters the incoming received signal into the three bands of interest. A bank of low noise amplifiers 461-1, 461-2, 461-3 one for each band of interest 403-1, 403-2, 403-3 provides respective receiver channels to transceiver 480 for processing.

The transceiver 480 may consist of suitable filters and synthesizers to generate the radio frequency chirp signals that drive the transmit side and filters and detectors to discern the presence of NQR signals of interest. Resistive couplers 405-1, 405-2, and 405-3 may also be implemented to provide reference signals to the transceiver 480. It is understood that the transceiver includes suitable analog-to-digital converters and digital analog converters and incorporates digital signal processors and frequency synthesizers for the stated purposes. More details of the transceiver design and processing algorithms are in the co-pending patent applications referenced elsewhere.

FIG. 4B is a high level schematic diagram of an electrical circuit showing an embodiment of the portal shield, slab radiator and single strip line coupler. The transmit signal 220 is provided to the portal 101 such as via a coaxial cable 492. The signal is then fed to a balun 493 which in the preferred implementation may provide a 4 to 1 impedance transformation between the 50 ohm characteristic impedance of the coax 492 and the desired 12.5 ohm characteristic impedance of the slab radiator 494. The strip line coupler structure 495 is also shown, in board of the left side slab radiator 494-L. The coupling resistors 496 at the roof of the portal are also shown between the two slab sections 494-L, 494-R.

Energy emitted via the slabs (see 110 in FIG. 1) induces the quadrupole resonance effect in a material within the portal which is then picked up by the strip line coupler 495 (120 in FIG. 1) disposed within the portal. The response signals are fed through coax 451 providing the receive signal to the transceiver.

Figure 4D:
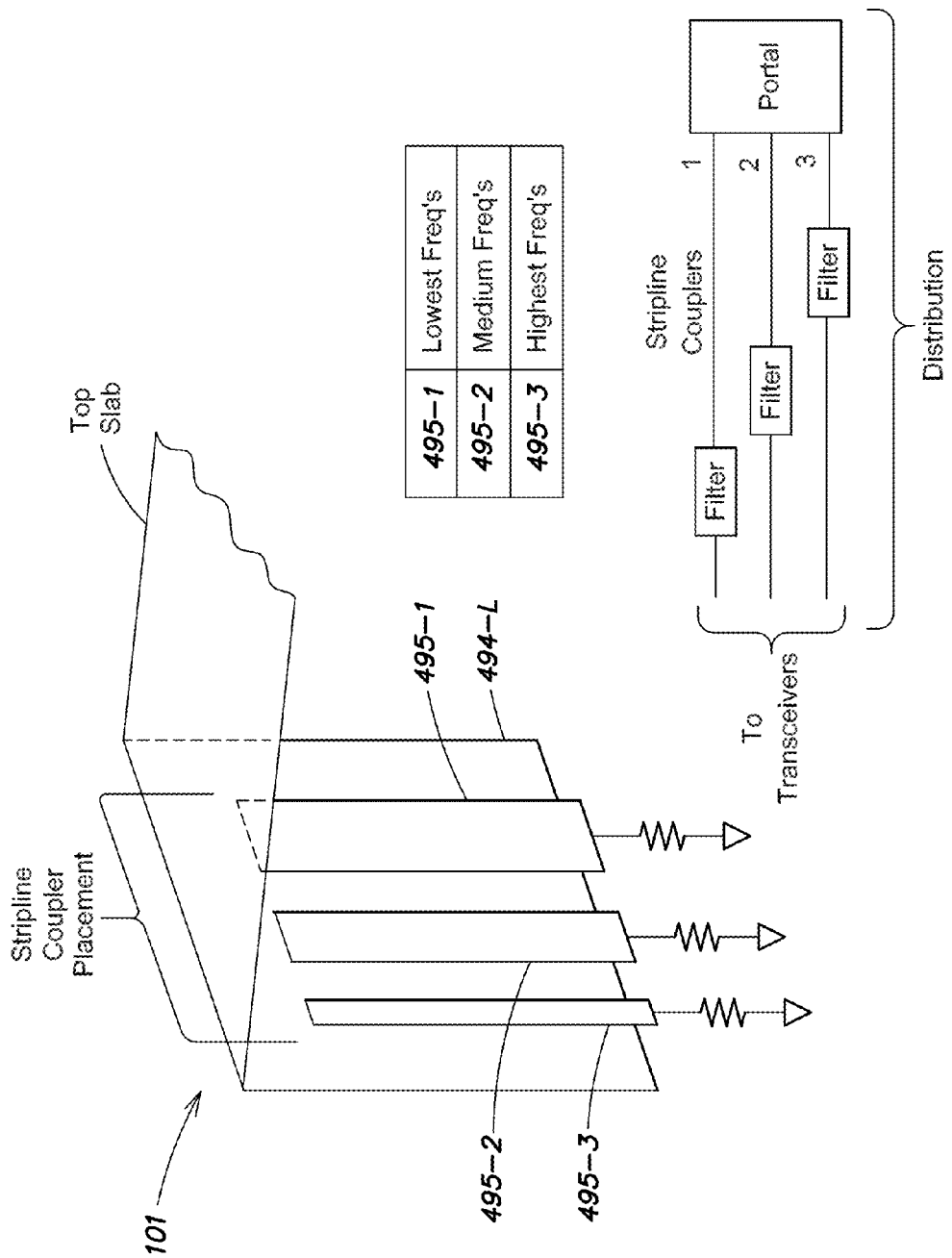

FIG. 4D shows portions of a slightly different arrangement where three receive couplers 495-1, 495-2, 495-3 are provided such that a respective coupler is designed to handle one of the frequency bands of interest. This partially cutaway isometric view shows an arrangement with the three couplers disposed in board of the left side slab within the portal.

Relative widths of the strip line type couplers may vary and depend upon the frequency band of interest. The widths range in size from a relatively thin coupling strip 495-3 intended to cover the highest frequencies, a midrange width strip 495-2 to cover the middle frequencies and a relatively wider strip 495-1 to cover the lowest frequency range. In this application the strip line couplers individually feed a respective receive filter and thus a receive triplexer is not needed.

Figure 4E:
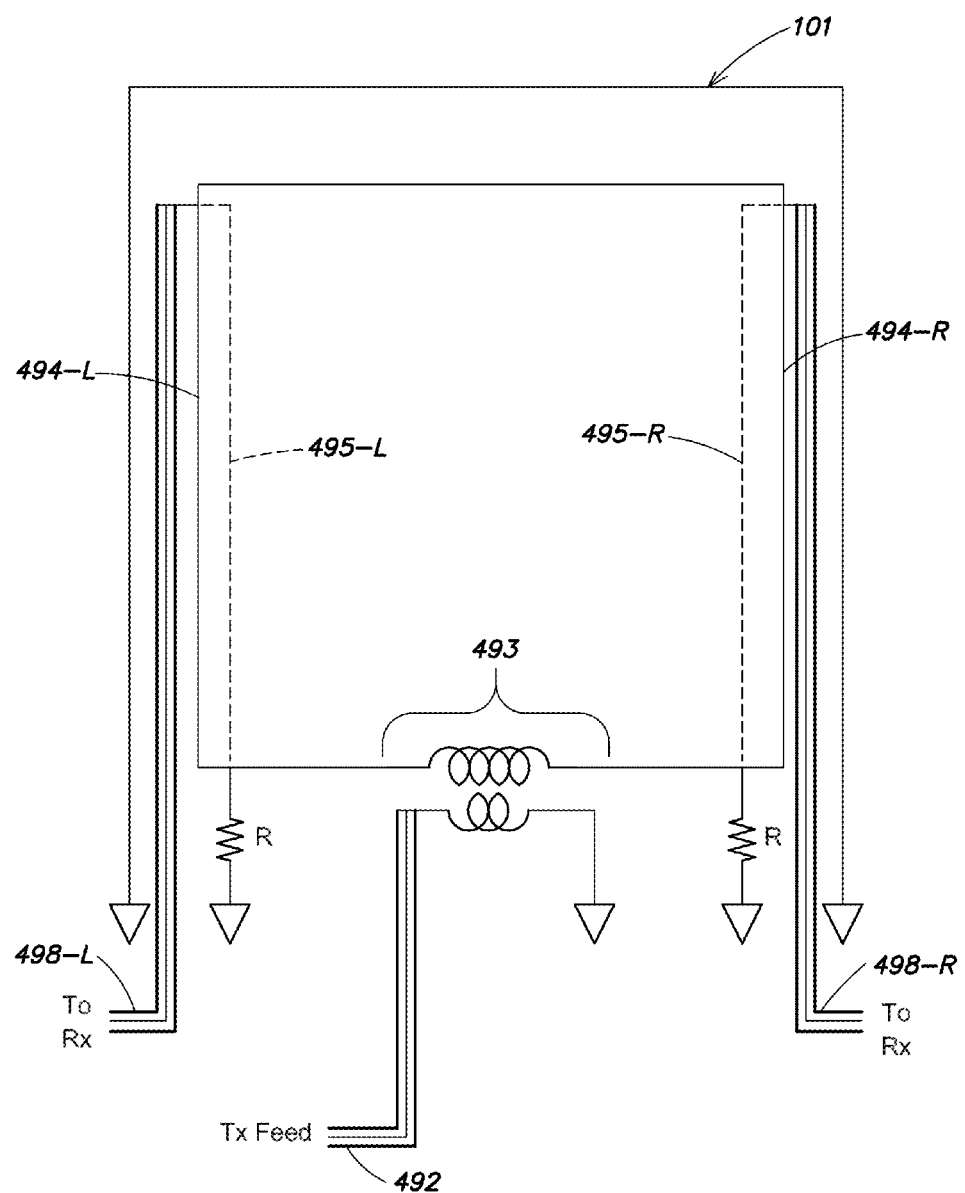

FIG. 4E is yet another implementation where mirror image strip line couplers 495-L, 495-R are disposed on the left and right sides of the portal. Thus a first coupler 495-L is placed on the left side of the portal and a second coupler 495-R is placed on the right side of the portal, each inboard of a respective slab radiator side. The two strip line couplers respectively provide outputs 498-L and 498-R; the two outputs can then be processed in a couple of different ways. If the two outputs 498-L and 498-R are kept separate, they may be fed to respective analog-to-digital converters in the receiver. This configuration can be used to coherently add the two responses making the combined strip line couplers response more uniform across the portal. However the receiver processing can also compare the response of the left hand coupler to the right hand coupler, providing information about the relative location of the detected material in the left to right direction within the portal. This information can be added to height information, such as derivable via the techniques described below, to provide information about the location of the detected material both in the left to right and bottom to top direction within the portal.

In a different configuration, the left and right stripline coupler 495-L, 495-R outputs can be combined such as with a differential amplifier or a non-ferrite 180° hybrid circuit, before receiver processing. This combination loses left to right position information, but does provide improved performance over the use of a single strip line coupler, since the combined strip line coupler response is expected to be more uniform across the portal.

4. Wideband Chirps Encompass Multiple NQR Resonances

Figure 5A:
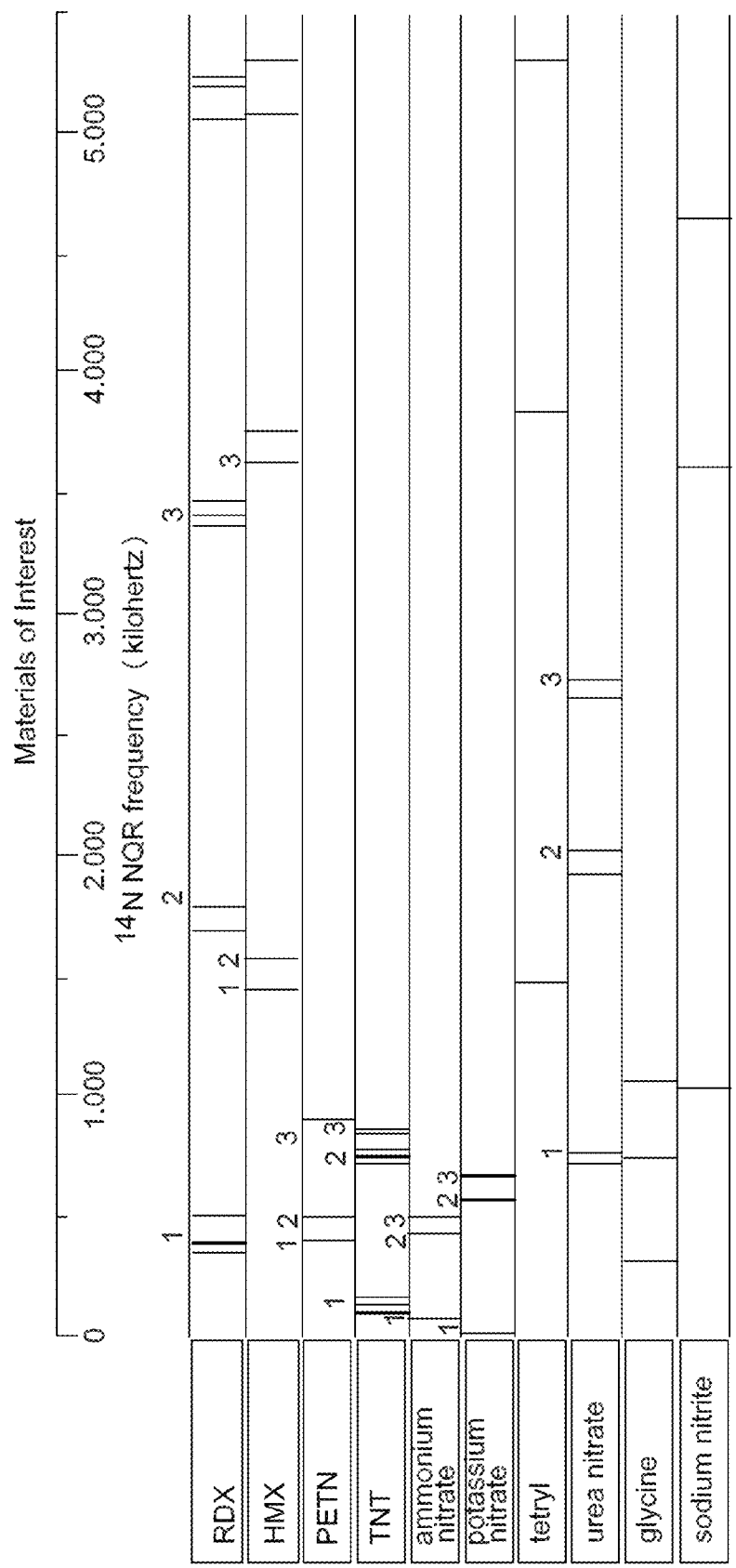
FIGS. 5A-5D show chirp signal and filter bandwidths for a three-channel implementation.

FIG. 5A is a prior art published plot of expected spectral response of NQR resonance lines for various nitrogen-based explosive and nonexplosive materials. The chart can be used to identify multiple resonance lines of interest for each material. The x-axis indicates resonance lines corresponds to the resonance frequencies of interest and/or groups of resonances of interest for specific materials. In one arrangement, the system uses these NQR resonance characteristics to determine which material(s) are present in the portal.

In one implementation, the system 100 makes use of three radio frequency transceiver channels. It is therefore desirable to divide the set of NQR frequencies of interest into three bands each including multiple resonances of interest. The spacing of the resonances excited by a given chirp should be sufficiently far apart enough so that the matched filters in the detectors can discern each NQR resonance. The preferred design is also such that the three chirps may overlap in time so that any given point in time it may be case that two or even three resonances are being excited.

Figure 5B:
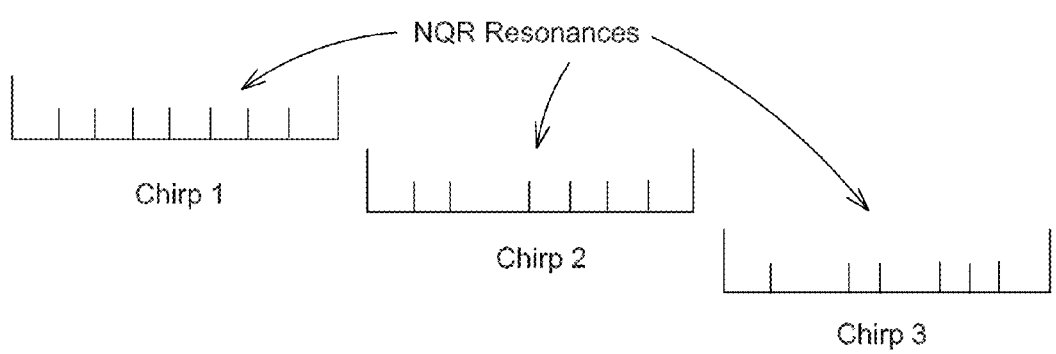

This arrangement can be represented by the chirp plots of FIG. 5B. The chirps are preferably linear frequency modulated continuous chirps generated and detected according to the techniques described herein and/or per the above referenced co-pending patent applications.

As explained above, multiple Digital to Analog Converters (DACs) and amplifiers operating in parallel generate multiple simultaneous chirp signals at the same time. Having the capability of generating more than one chirp simultaneously at a given time helps minimize the overall time needed to detect the possible presence of multiple materials. Minimizing the processing time can be important in an environment where human beings are being asked to walk through the portal, such as in an access control application of the system.

Figure 5C:
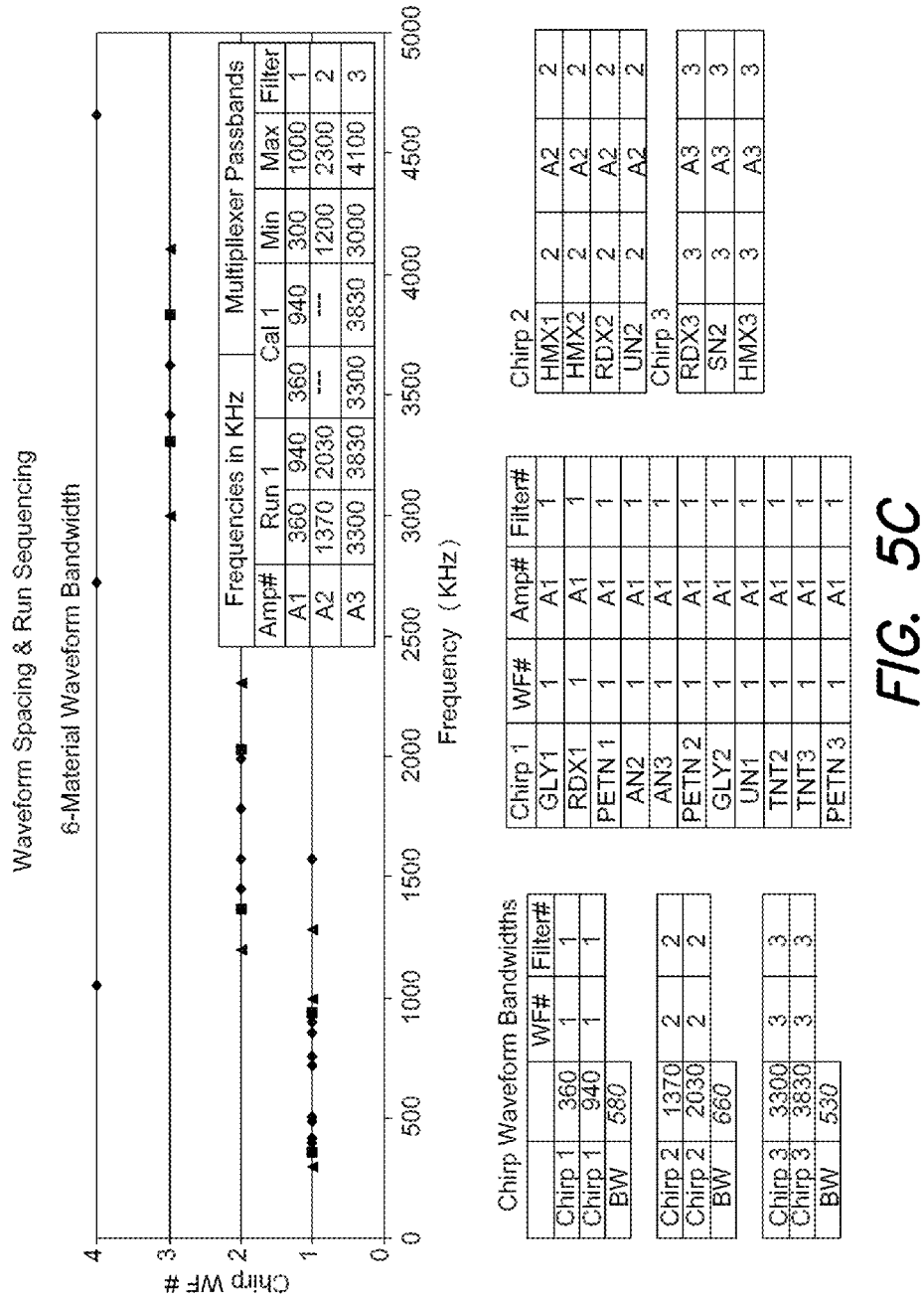

A chart such as that shown in the top portion of FIG. 5C can then be used to s develop a start and stop frequency plan for each of the three wideband chirps. This tables list, for each of six materials of interest, three or more NQR resonances of interest. As one example, the material RDX has NQR resonances in a first band of interest from 360 to 940 kHz (RDX1), a second band of interest from 1370 to 2030 kHz (RDX2), a third band from 3300 to 3830 kHz (RDX3). A glycine material has two resonances of interest in the 360 to 940 kHz (GLY1), 685-725 kHz (GLY2), and 1370 to 2030 kHz (GLY2). Other materials have similar assignments to bands.

The next aspects of chirp waveform generation are also shown in FIG. 5C. The table in the upper portion of the figure is a graphical view of a chirp signal generation plan or schedule for multiple "runs" of the system. The chart is developed from information in the lower tables, with the proviso that it is possible to excite more than one NQR per chirp, as long as the receiver matched filter can discriminate adjacent resonances.

The bottom right hand side of FIG. 5C also illustrates resulting tables that define three run sequences (labeled chirp1, chirp2 and chirp3). Selected chirp waveform bandwidths may then be as shown in the bottom left side table, with the first chirp ranging from 360 to 940 kHz, the second chirp ranging from 1370 to 2030 kHz, and the third chirp ranging from 3300 to 3830 kHz.

Figure 5D:
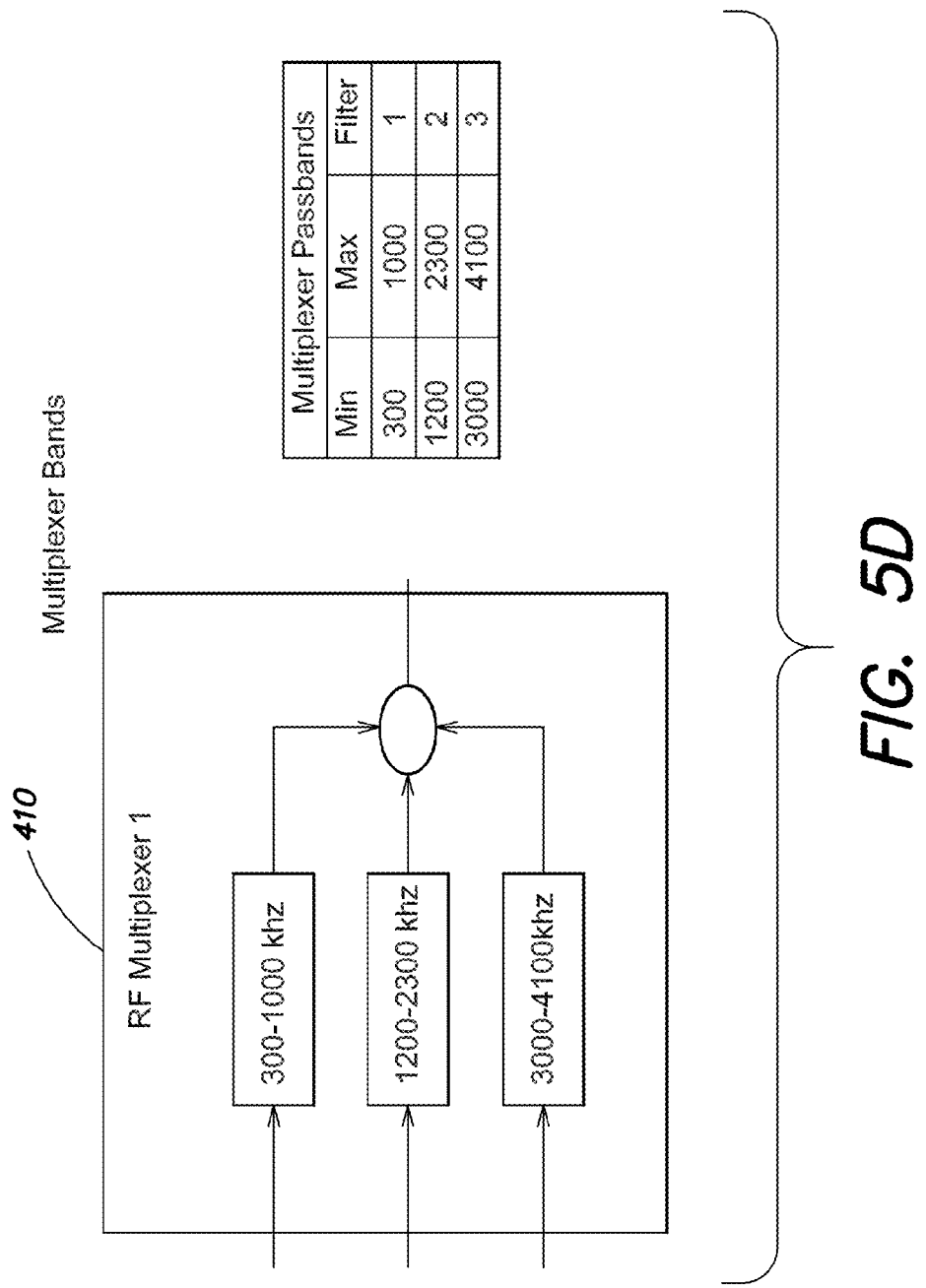

The multiplexer 410 passbands for each chirp is shown in detail in FIG. 5D. These can include respective filters with a 300-1000 kHz passband, 1200-2300 kHz passband, and 3000-4100 kHz passband. Also of importance is to note this dictates a minimum and maximum frequency range over which each amplifier in each channel in the system is expected to operate.

It should be noted that it may not be best to generate sweeps for each possible resonance line of interest shown in FIG. 5A. Here for example the designer has determined that chirp generation within some frequency range(s) does not easily fit all possible resonances for all materials. The designer thus has selected some resonances to be eliminated from the chirp sequencing plan.

Waveform run sequencing table(s) such as that shown in the bottom portion of FIG. 5C can then be developed for use by the PC 150 in controlling the input to the D/As 152. The tables list the start and stop frequencies for each of the three chirps that are to be generated. One of the three available D/As, low pass filter, and amplifier sets can then be assigned an associated one of the chirps per the sequencing in the table.

Thus it is now understood how it is possible to ensure that multiple resonances are tested in different bands at the same time resulting in a sequence of runs which are optimized for testing multiple materials of interest, to minimize analysis time, while also observing a constraint that no more than one resonance for each material of interest is excited at any one point in time.

It should be understood that this "three channel, wideband chirp" architecture for signal generation and detection may be used with the slab type portal of FIG. 2A-2H herein, or the individual wire loop type portal described below in connection with FIG. 13 or FIG. 16 or as in the other co-pending patent applications referenced above.

5. Magnetic Amplification via Three Port Directional Coupler with Ferrites

Figure 6A:
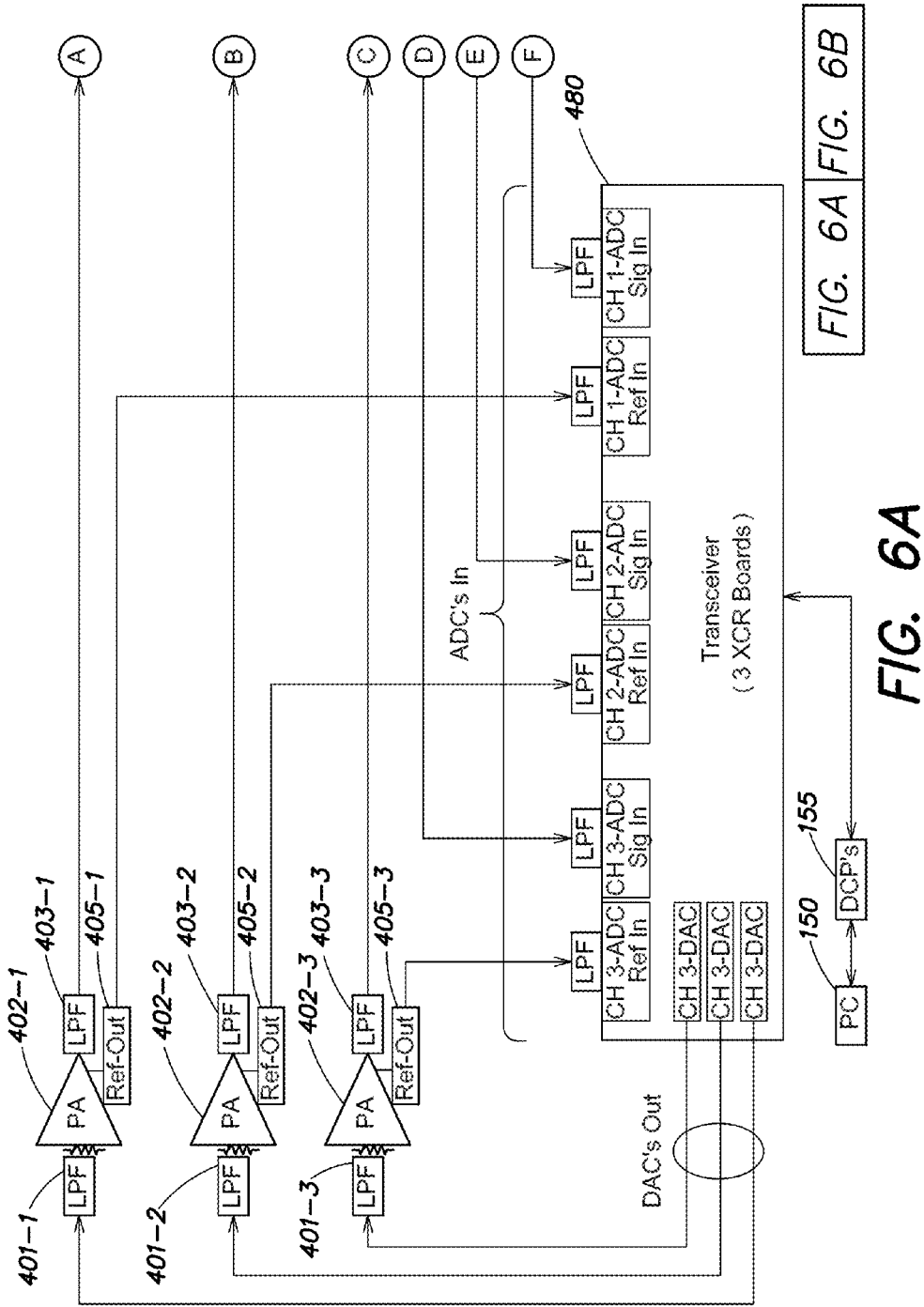
FIGS. 6A-6E are an alternate arrangement using the slab radiator with a directional coupler to provide magnetic amplification of received signals.
Figure 6B:
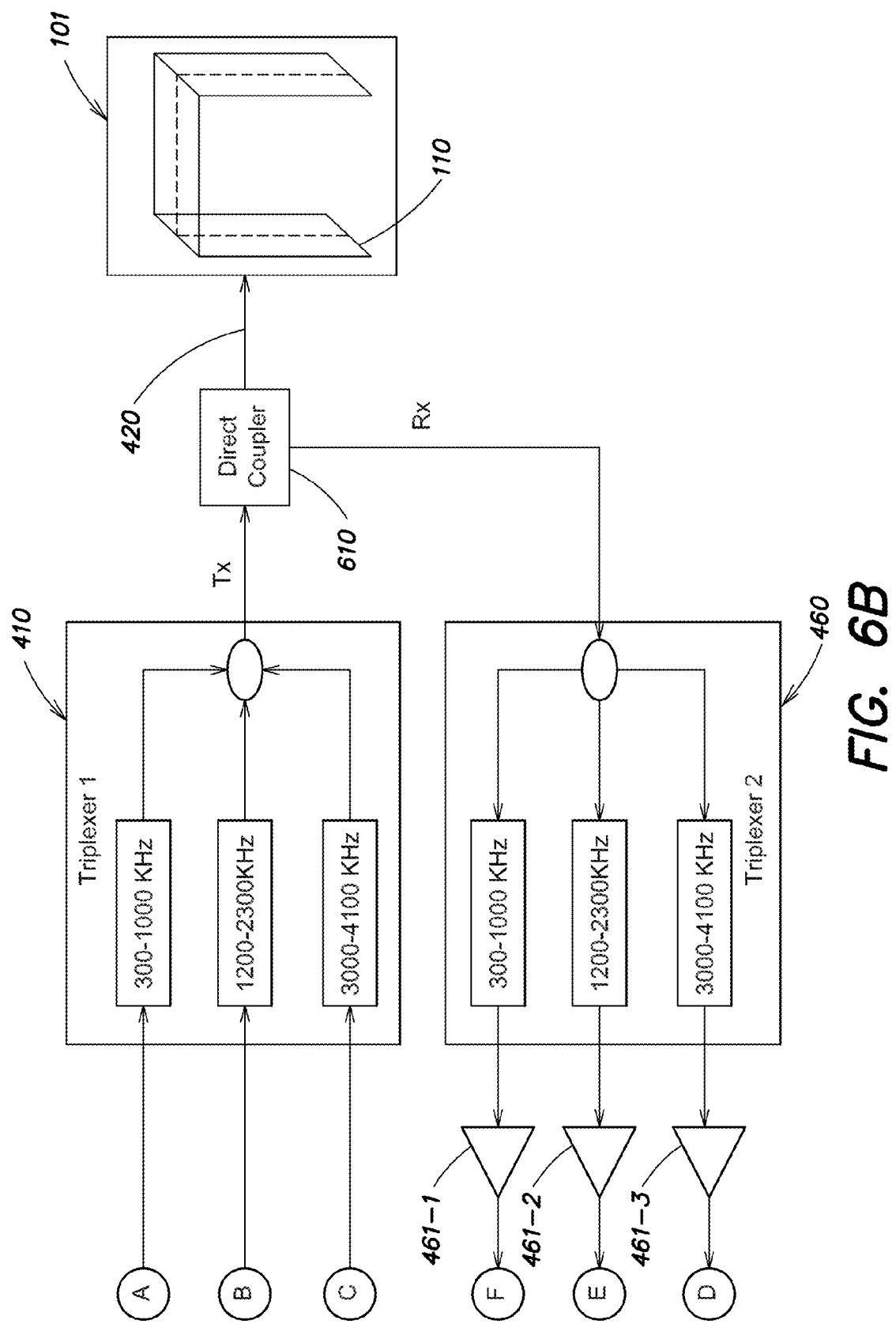

In other embodiments the receive and transmit radiators may be combined. In these implementations, there may be a one or more such radiating elements disposed within the portal that are each used for both the transmit and receive signal paths. FIG. 6A is one example showing the RF signal processing circuits and transmit and receiver circuitry analogous to that shown and described in connection with FIG. 4A above. The difference in this implementation, is that a directional coupler 610 is disposed between the transmit path, the portal radiating elements and the receive path. The combined transmit and receive radiating elements may have also be slabs or wire conductors.

The illustrated three port directional coupler 610 separates signals based on the direction of signal propagation. These devices are used to unequally split the signal flowing line and to fully pass the signal flowing in the opposite direction. In an ideal situation some portion of the signal flowing into the receive port will appear at the coupled port (that is, the port used to feed the radiator). Likewise any signal flowing into the coupled port will be coupled fully to the receive port. However, the transmit port and the coupled port are isolated in that any signal flowing into the transmit port will not appear at the coupled port but will feed through to the receiver port.

Figure 6C:
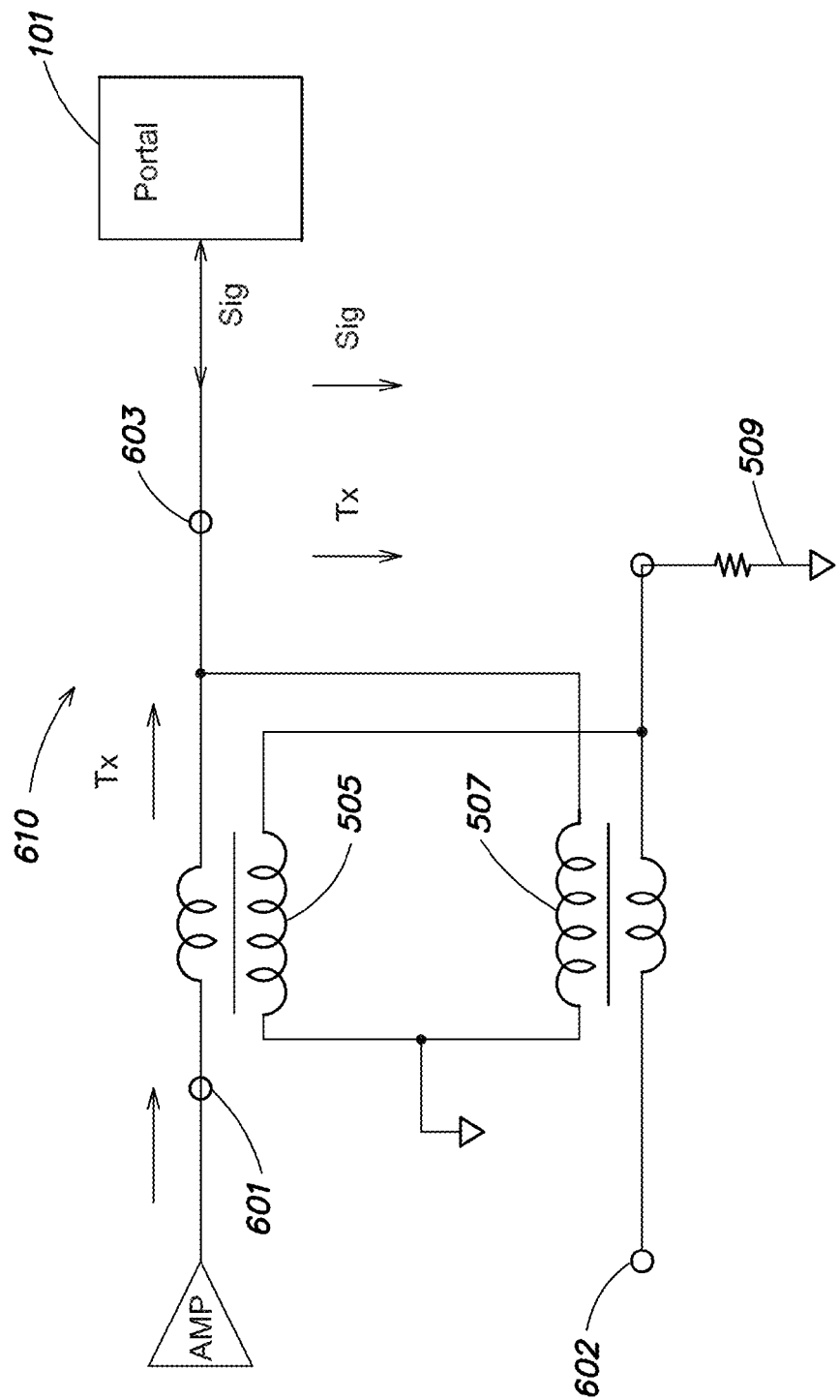

The three part directional coupler may be realized by two transformers 505, 507 connected as shown in FIG. 6C. Each transformer includes a pair of windings separated by a magnetic material such as a ferrite. Directional couplers of this type are "impedanceless," in that they become 50 ohm, directional couplers simply by matching all ports to 50 ohms, respectively.

The coupler 610 has three operating ports. A first port 601 receives a signal from the transmit amplifier feeding it to a first coil of the first transformer. The other terminal of the first coil is then also fed to the radiating element in the portal as the common port 603. The signal returned from the radiating element in the portal of receive port 602 is thus fed to the first coil of the first transformer as well as a first coil of the second transformer 507.

One terminal of the secondary coil of each transformer is fed to a common ground reference point. The other terminal of the first transformer 505 is fed to an isolation port which provides a termination point to ground through a load resistance. The remaining terminal of the second transformer 507 provides the coupled port (602) output to the receiver.

Figure 6D:
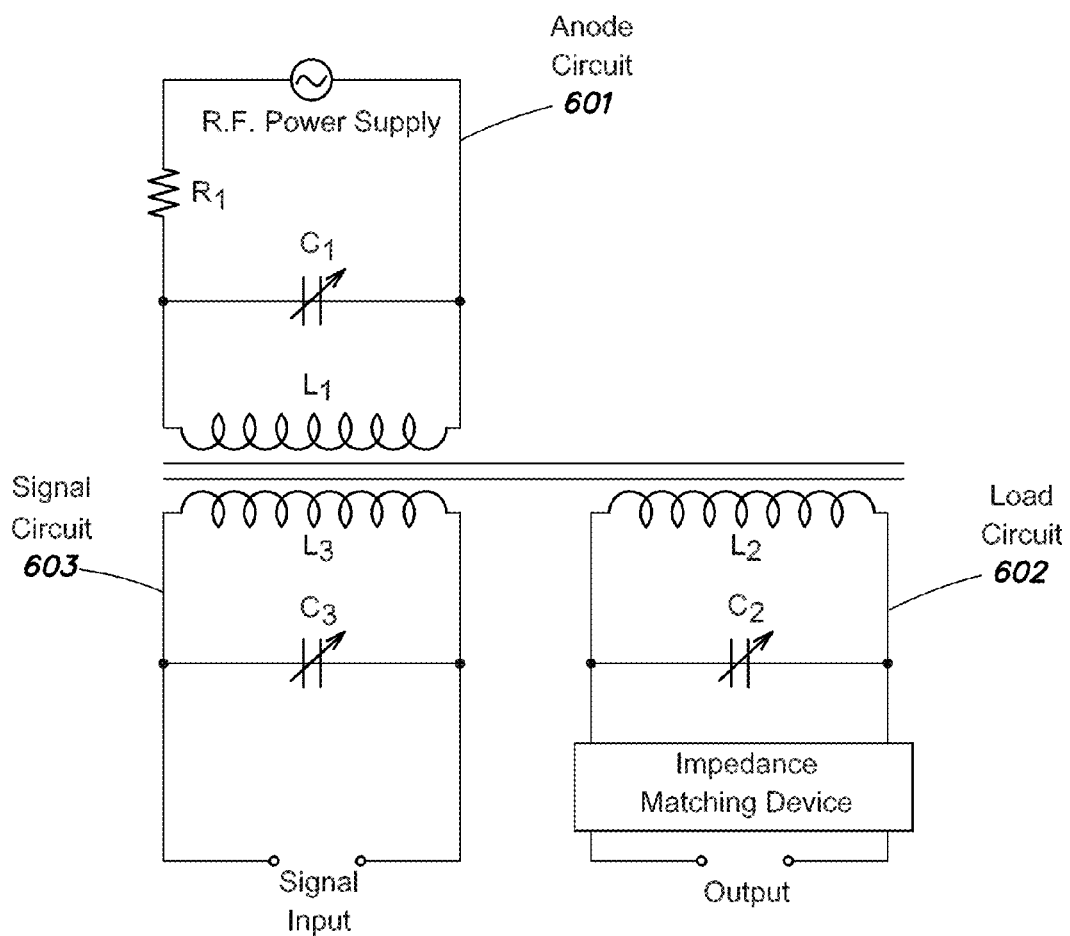

We have realized that this type of transformer-based ferrite coupler can be considered to operate as a magnetic amplifier for radio frequency signals. FIG. 6D maps the functions of a magnetic amplifier to the various ports of the directional coupler. For example the anode circuit in the magnetic amplifier corresponds to the functions of the transmitter port (601). The load circuit in the magnetic amplifier operates as port (602) fed to the receiver, and the signal circuit in the magnetic amplifier operates as the common connection port (603) which is fed to the portal radiator.

Figure 6E:
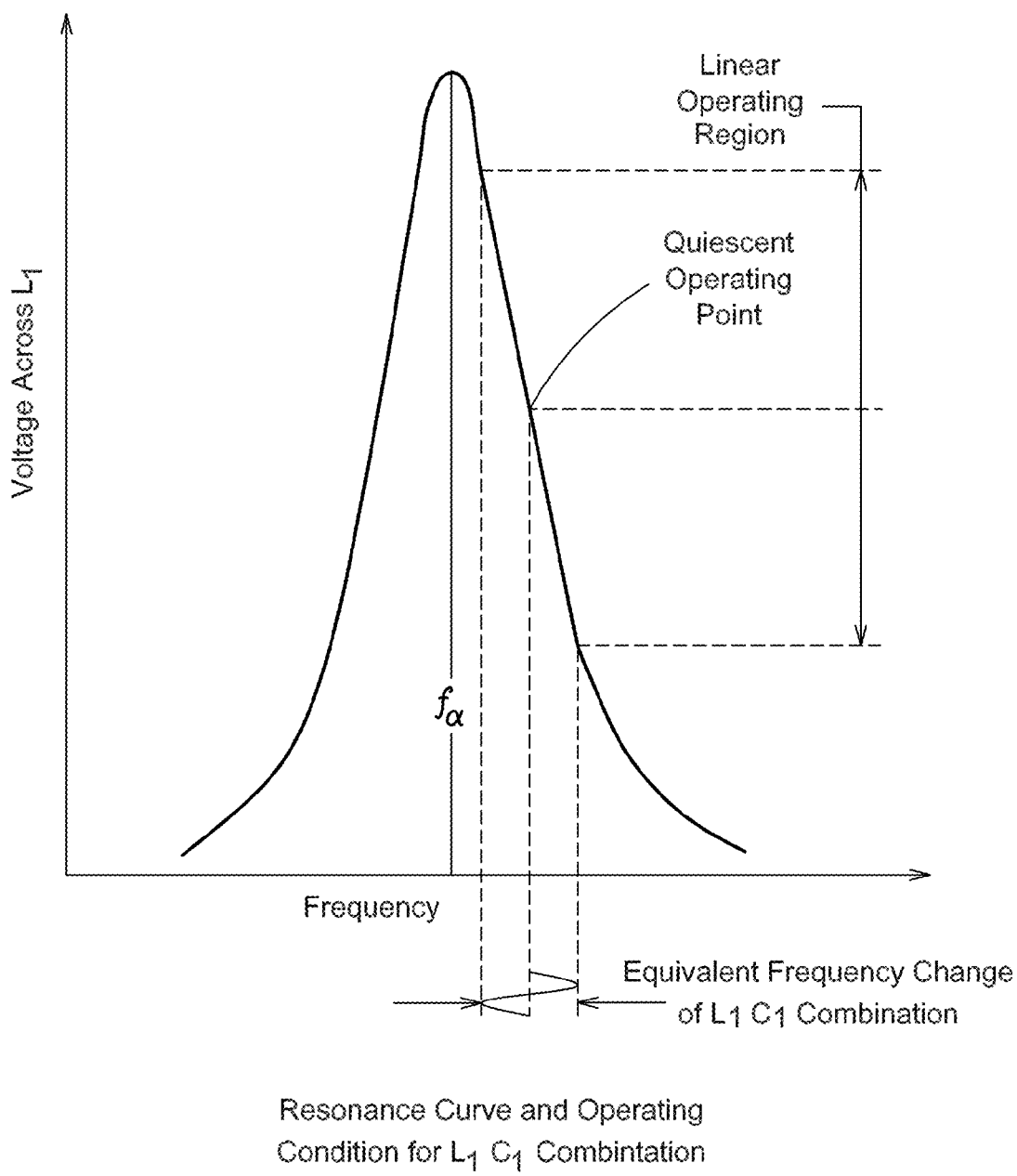

As known in the art and shown in FIG. 6E, the resonance curves and operating condition can be set such that the quiescent operating points exhibit amplification in an is approximately linear operating region. In this configuration the input signal sets, with the ferrite, where the magnetic amplifier will operate on the hysteresis curves.

In the preferred embodiment, if directional coupler transformer-based directional couplers make use of magnetic core transformers and winding pairs, it can operate as a magnetic amplifier, providing a higher signal-to-noise ratio than one would otherwise expect. The ferrite directional coupler implementation does require feedback or other temperature or humidity stabilization in order to obtain adequate receive signal power. This arrangement therefore may or may not be preferred in all instances over the use of separate slab and stripline couplers without ferrites and with low noise amplifiers.

6. Waveform Sequencing Including Multiple Simultaneous Chirps

As mentioned above, a system architecture that uses multiple Digital to Analog Converters (DACs) and amplifiers operating in parallel may be used to generate multiple simultaneous chirp signals at the same time. Having the capability of generating more than one chirp simultaneously at a given time helps minimize the overall time needed to detect multiple materials. Minimizing the processing time can be important in an environment where human beings are being asked to walk through the portal, such as in an access control application of the system.

However, even when there may be multiple materials of interest, and the capability of generating more than one chirp signal at a time exists, it can be desirable that only one resonance per material is excited any given point in time. At least one reason for this is the relaxation time (T1) necessarily observed for detecting an NQR response. However, tuning the six DACs and bandpass filters to different bands of interest for different materials at any given instant in time permits collecting at least partial information about different materials of interest simultaneously. Thus in some implementations, a waveform spacing, run plan, and corresponding arrangement of passband filters observes these constraints.

Figure 7:
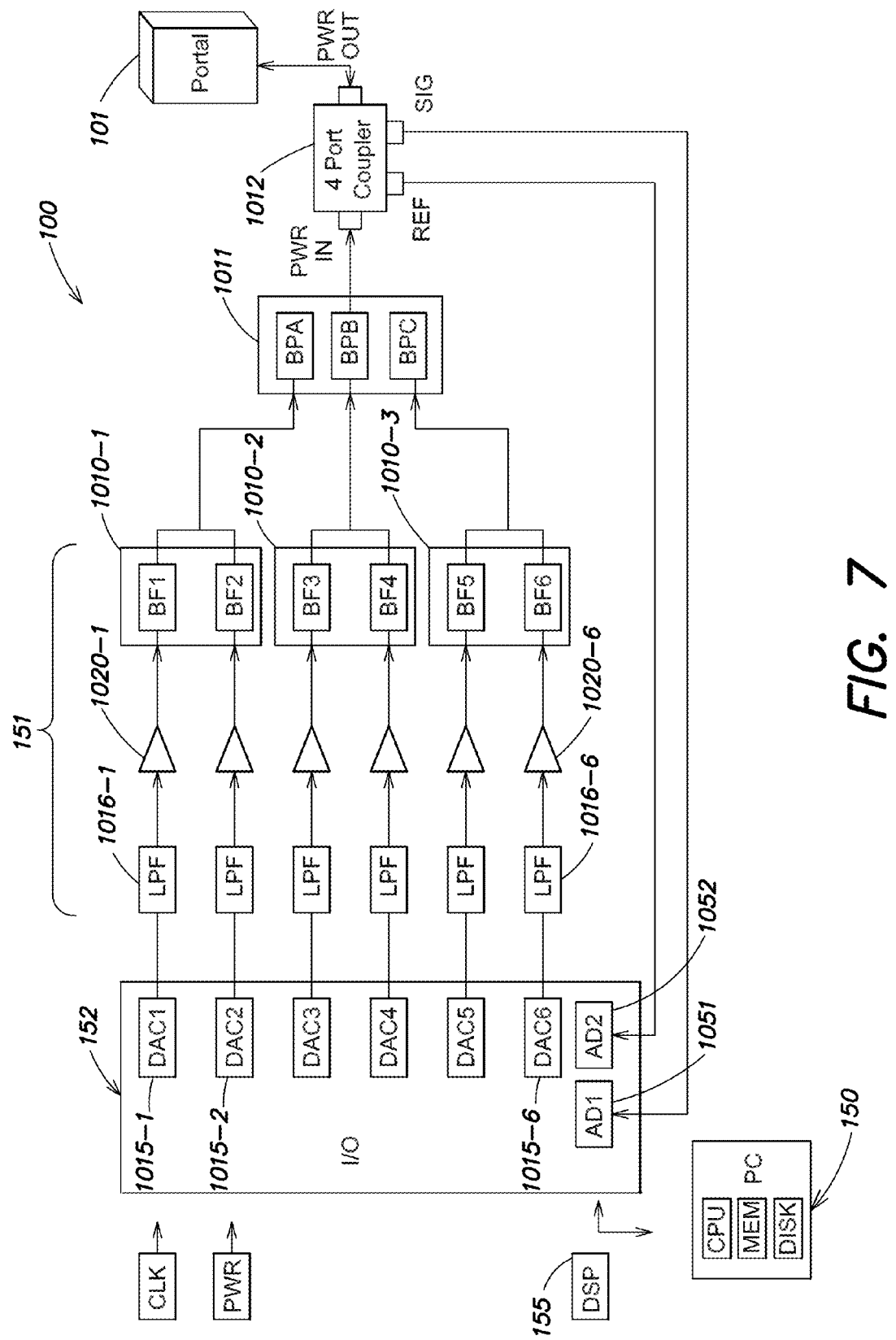
FIG. 7 is a high-level block diagram of a three channel NQR detection system.

In this arrangement shown in FIG. 7, similar to those of FIGS. 4A and 6A, an NQR system uses a PC 150, DSP(s) 155, and a portal 101 as before. An input/output (I/O) transceiver subsystem, which may be a peripheral board plugged into the PC via an suitable interface includes a number of digital to analog converters (DAC1 to DAC6)) 1015-1, . . . , 1015-6 and analog to digital converters (AD1 and AD2) (1051, 1052).

In the transmit direction, the PC controls the multiple DACs 1015-1, . . . , 1015-6 to generate the desired chirp signals that include one or more NQR frequencies of interest. More particularly, each of many RF signals may include a linear chirp signal, for example, a sinusoidal signal having an instantaneous frequency that changes linearly with time.

As before, the chirp signals preferably originate as digital signal data computed and/or stored by the Personal Computer 150. Each digital chirp signal, associated with one or more NQR frequencies of interest, is fed to one of the DACs 1015, is low-passed filtered, and amplified. Multiple analog chirp waveforms with alternating power state illuminations may be generated at a given instant in time via the multiple DACs 1015-1, . . . , 1015-6, filters 1016-1, . . . , 1016-6, and amplifiers 1020-1, . . . , 1020-6 operating in parallel. As will be explained in greater detail, there is a specific desired characteristic of the order in which these analog chirp signals are generated to maximum efficient use of the system while avoiding undesirable effects in the resulting NQR responses.

In this arrangement, the DACs 1015 produce six (6) signals that are then filtered and amplified before being combined via a set of three diplexer filters 1010-1, 1010-2, 1010-3 (BP1, BP2) (BP3, BP4) (BP5, BP6) and a triplexer 1011 (BPA, BPB, BPC). Each of the diplexers 1010 may contain two (2) bandpass filters; the first diplexer having bandpass filters BP1 and BP2, the second diplexer having bandpass filters BP3 and BP4, and the third diplexer having bandpass filters BP5 and BP6. The triplexer 1011 may also include a set of three bandpass filters BPA, PBB, and PBC to provide the resulting radio frequency (RF) excitation signal that includes up to six simultaneous chirp signals.

The output of the triplexer 1011 is fed to the PWR IN port of a 4-port coupler 1012 in this arrangement. The PWR OUT port of the 4-port coupler is connected to the portal 101 via wire conductors (transmission lines) or slabs disposed within the portal. The signals returned from the 4-port coupler, including the SIG response from the portal and a REF signal detected from the input coupler itself are fed to corresponding analog to-digital converters 1051, 1052 (AD1 and AD2) to provide digital response signals back to the personal computer for signal processing. The digital receiver processing implemented DSP 155 may include down conversion, demodulation (dechirping), matched filtering, and other detection processing. More details of the portal design, excitation wire loops, signal generation, detection and processing, as well as alternative system architectures and components are also described in the patent applications that were incorporated by reference above.

The architecture shown here uses six amplifiers 1020-1, 1020-2, . . . , 1020-6 feeding the three diplexers 1010 and a triplexer 1012 allows up to six chirp signals to be introduced through the 4-port coupler 1012 to the portal 101 at the same time. Having the capability of generating more than one chirp simultaneously at a given time helps minimize the overall time needed to detect multiple materials. However, even when there may be multiple materials of interest, and the system physically provides the capability of generating more than one chirp signal at a time, it can be desirable that only one resonance per material is excited any given point in time. At least one reason for this is the spin relaxation time (typically referred to as "T1" in the NQR literature) that is necessarily observed for detecting an NQR response. However, tuning the six DACs 1015-1, 1015-2, . . . , 1015-6 and bandpass filters 1016-1, 1016-2, . . . , 1016-6 to different bands of interest for different materials at any given instant in time permits collecting at least partial information about at least some of the different materials of interest simultaneously.

Figure 8A:
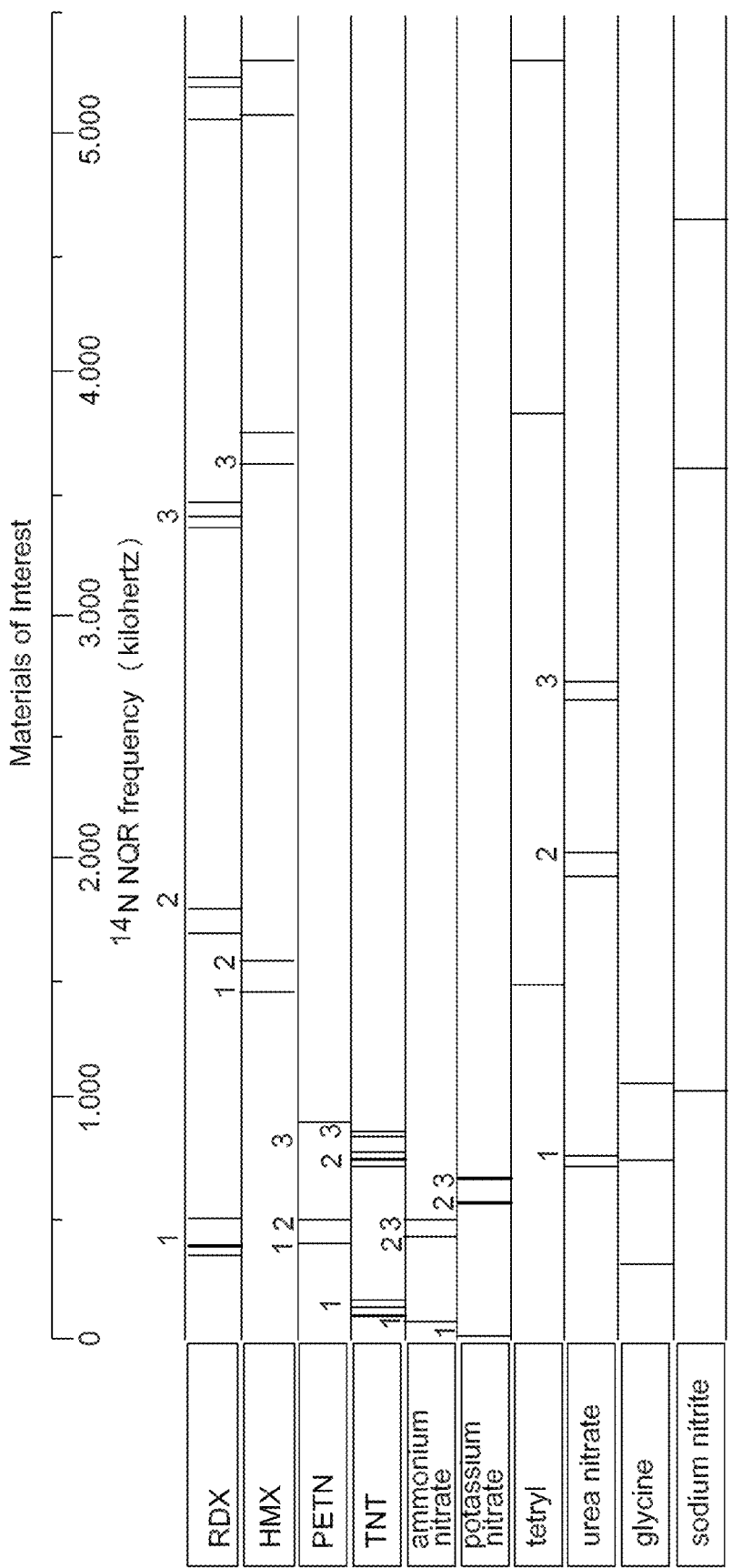
FIG. 8A is a plot of expected sets of NQR resonances for various materials of interest.

FIG. 8A is a prior art published plot of expected spectral response of NQR resonance lines for various nitrogen-based explosive and nonexplosive materials. The chart can be used to identify multiple resonance lines of interest for each material. The numerical designation above each material resonance line corresponds to the resonance frequencies of interest and/or groups of resonances of interest.

A chart such as that shown in FIG. 8A can be used to develop a table such as that shown in FIG. 8B. This table lists, for each of nine materials of interest, three or more 40 kHz frequency bands that contain NQR resonances of interest. As one example, the material RDX has NQR resonances in a first band of interest from 365-405 kHz (RDX1), a second band of interest from 1765-1805 kHz (RDX2), a third band from 3390-3430 kHz (RDX3), and a fourth band from 5005-5045 kHz (RDX4). A glycine material has resonances of interest in the 280-320 kHz (GLY1), 685-725 kHz (GLY2), and 1030-1070 kHz (GLY3) bands.

Figure 9A:
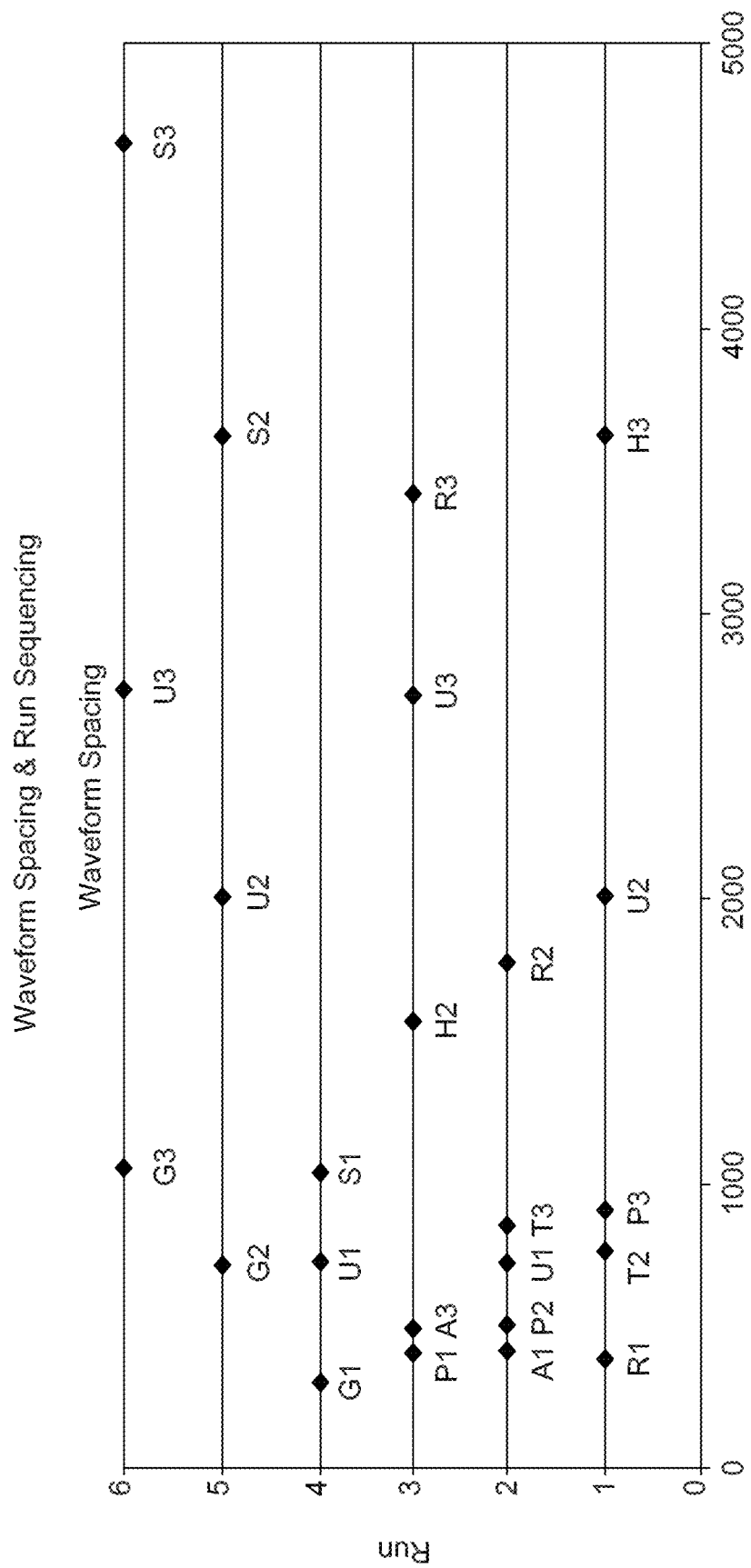

The next aspects of chirp waveform generation are shown in FIGS. 9A and 9B. The chart in the upper left of the figure is a graphical view of a chirp signal generation plan or schedule for multiple "runs" of the system. The chart is developed from information in the table of FIG. 8B, with the provision that although it is possible to generate up to six possible chirps for any run, the constraint must be observed that the NQR response for only a single material of interest can be excited for that run. A resulting graphical depiction of runs (numbered 1 through 6) versus center frequency can be developed for each resonance of interest for the set of materials of interest.

The right hand side of FIG. 9A illustrates resulting tables that define six run sequences, a first set of three runs for explosive materials of interest (labeled Run1, Run2, and Run3), and three "calibration" runs for non-explosive materials (labeled Cal1, Cal2, and Cal3). For example, Run1 will generate five 40 kHz chirps (to detect RDX1 from 365-405 KHz, TNT2 from 730-770 kHz, PETN3 from 875-915 kHz, UN2 from 1980-2020 kHz, and HMX3 from 3600-3640 kHz).

It should be noted that it may not be best to generate sweeps for each resonance line of interest. Here for example the designer has determined that the lowest resonance lines for ammonium nitrate and TNT occur in a range of from 100-140 kHz. Since chirp generation within that range does not easily fit the design plan, they has been eliminated from the run sequencing plan.

A waveform run sequencing table such as that shown in the bottom left portion of FIG. 9A can then be developed for use by the PC in controlling the input to the DACs. That table lists the center frequencies for each of the chirps that are to be generated for that run. One of the six available DACs, low pass filter, and amplifier sets can then be assigned an associated one of the chirps per the sequencing in the table.

For example, during Run1, DAC 1015-1 (A1) can be assigned to generate a 40 kHz chirp centered at 385 kHz (that is, sweeping from 365-405 kHz as indicated in the Run1 table), DAC 1015-2 (A2) may be idle, DAC 1015-3 (A3) centered at 750 kHz, DAC 1015-4 (A4) centered at 895 kHz, DAC 1015-5 (A5) centered at 2000 kHz, and DAC 1015-6 (A6) centered at 3620 kHz.

Chirp generation assignments are also made by the PC for the other 5 runs (Run2, Run3, Cal1, Cal2, Cal3) as per the tables.

Also of importance is to note the minimum and maximum frequency range over which each amplifier is expected to operate. The Multiplexer Passbands table then determines the passbands associated with each leg of the three diplexers. For example, given the assigned frequencies across all possible runs, diplexer leg A1 (corresponding to filter BP1 in FIG. 7) which receives the output of DAC A1 should have a passband from about 270-440 kHz. Likewise diplexer leg A2 (BP2 in FIG. 7) associated with DAC A2 should have a passband from 460-530 kHz, diplexer leg B1 (BP3 in FIG. 7) from 670-785 kHz, diplexer leg B2 (BP4 in FIG. 7) from 815-1615 kHz, diplexer leg C1 (BP5 in FIG. 7) from 1735-2770 kHz, and diplexer leg C2 (BP6 in FIG. 7) from 3360-4690 kHz.

The outputs of the three diplexers 1010 are also sent to a corresponding leg of the triplexer. The rightmost two columns of the Multiplexer Passband table can be used to the passband for each leg of the triplexer. The first leg (BPA) should have a passband from 270-550 kHz, the second leg (BPB) from 650-1625 and the third leg (BPC) from 1700-4700 kHz.

Figure 10:
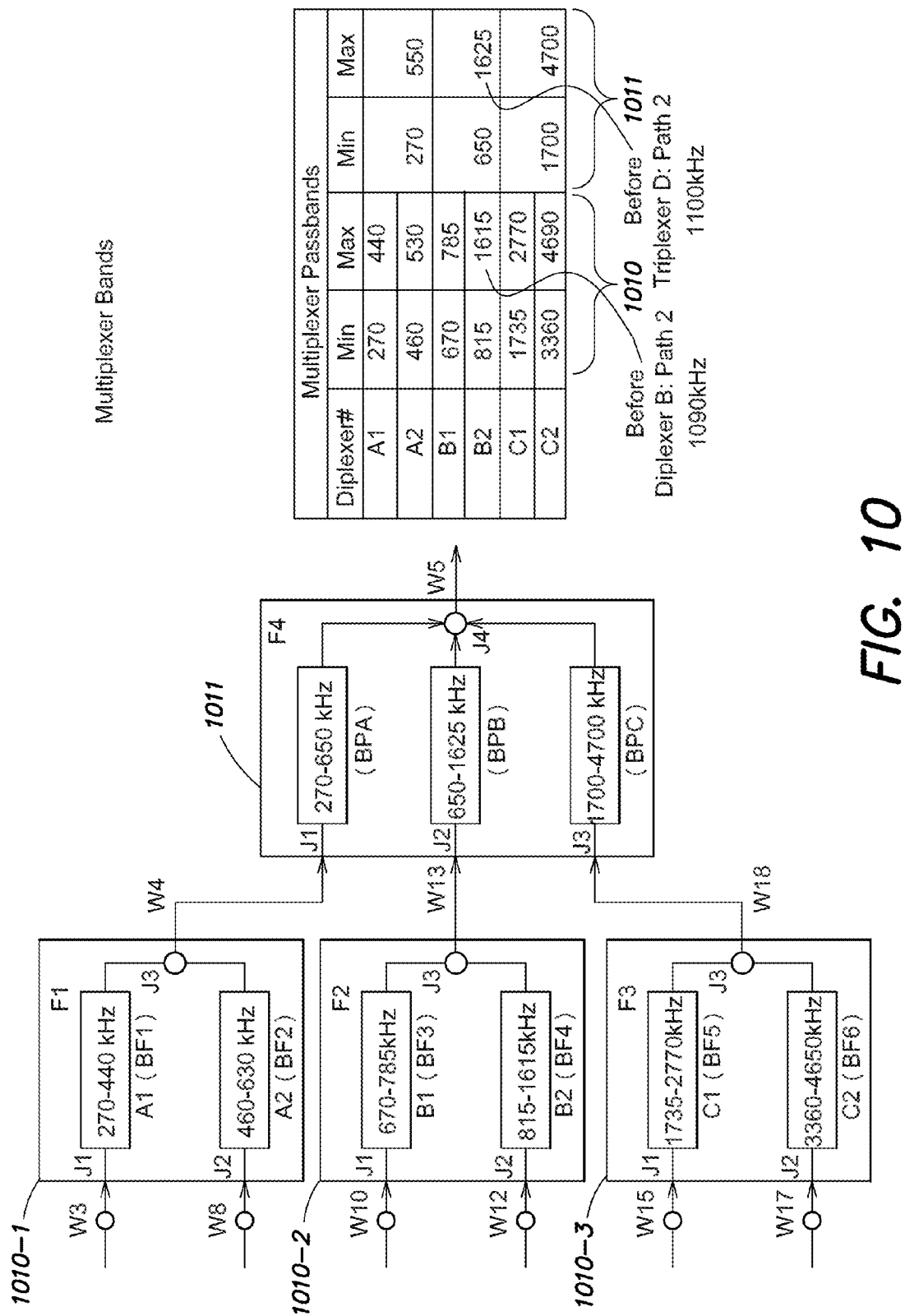
FIG. 10 illustrates the six-to-three channel multiplexer in more detail.

FIG. 10 illustrates the three diplexers 1010-1, 1010-2, 1010-3, the triplexer 1011, and the resulting passbands in more detail.

Thus it is now understood how it is possible to ensure that multiple resonances are tested in different bands at the same time resulting in a sequence of runs which are optimized for testing multiple materials of interest, to minimize analysis time, while also observing a constraint that no more than one resonance for each material of interest is tested for each run.

7. Four Port Coupler Design

It can also be discerned that a deterministic relationship exists between the signal used to excite the RF fields and the emitted response signal; this relationship depends on the transmitter circuitry used to generate RF fields. This relationship, if known, can further improve the performance of past detection signal processing. The directional coupler 610 thus may also produce a reference signal that is representative of path differences in the circuits used to generate the coherent RF emissions.

The coupler is thus in one embodiment a four port coupler that receives the transmit RF signal at an input port, and provides the RF signal at an output port. The emitted signal(s) from the portal are received at a signal port, but a reference signal is also provided at a reference port. The coupler may include one or more inductive and/or capacitive coupling circuits connecting the input port to the output port. The reference port may be provided by a circuit divider connected to the input port; the signal port may be provided by a circuit divider connected to the output port. The linearity of the coupler is further important due to the nature of the signaling methodology used here, which employs wideband chirps having multiple power levels. Any non-linearity introduced by the RF components in the system can cause error in the results. In order to ensure linear coupling, the use of ferrites is not desired due to intermodulation or distortion which can ensue if high enough power is applied.

Figure 11:
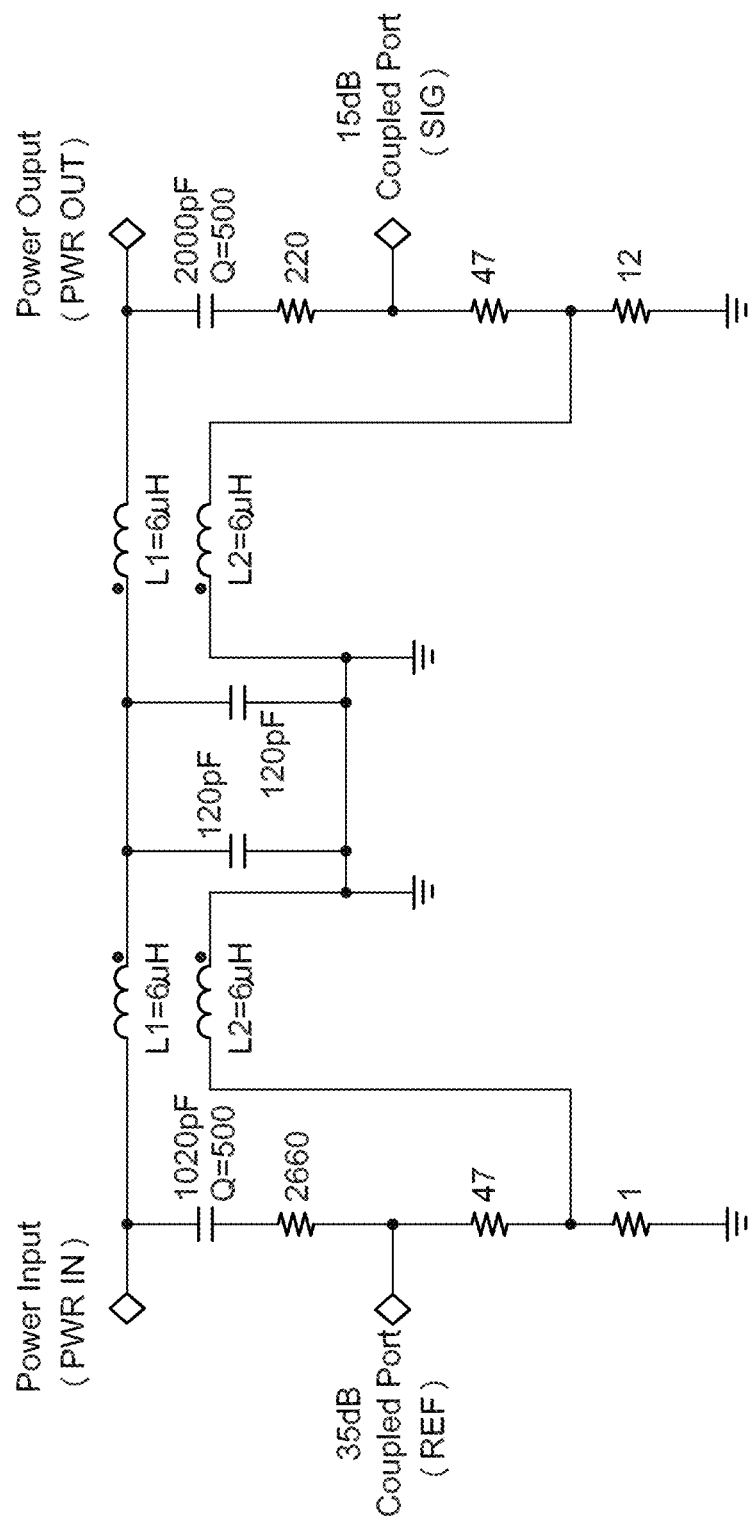
FIG. 11 is a more detailed diagram of a four port coupler used in some embodiments of the system.

FIG. 11 shows one implementation of a 4-port coupler 610 in more detail, preferably constructed from discrete components. The PWR IN and PWR OUT terminals correspond to those shown in FIG. 7. The 35 dB coupler port corresponds to the REF port of FIG. 7, and the 15 dB coupler port corresponds to the SIG port of FIG. 7. In general the PWR IN port is coupled to the PWR OUT port through a pair of series inductive (L1, L2=6 uH) and/or parallel capacitive circuits (120 pF) as shown. The REF signal is provided by a resistive coupling circuit connected to the PWR IN port. The resistive coupling circuit may include a series resistor divider (2680, 47 and 1 ohms) and series capacitor (1020 pF). Similarly, the SIG port is provided by a resistive coupling circuit which may be a resistor ladder (220, 47 and 12 ohms) and series capacitor (2000 pF).

8. Location of Materials Within Portal

It can also be discerned that a deterministic relationship exists between the signal used to excite the RF fields and the emitted response signal; this relationship depends on the transmitter circuitry used to generate RF fields. This relationship, if known, can further improve the performance of past detection signal processing.

More specifically, the RF circuitry may be connected to the conductive wires, transmission line(s), or slabs which start at a bottom portion of the portal, and extend up the sides thereof. With this arrangement, the relative phase of the response signal, when measured relative to the reference waveform, provides a measure of the vertical location of the material that caused the NQR response. This is because the fields generated within the portal are traveling wave fields in the vertical direction and the signals are stimulated emissions from the material of interest. The vertical location is expected to be a function of frequency and that function should therefore be measured and adapted for each NQR resonance of interest.

Figure 12A:
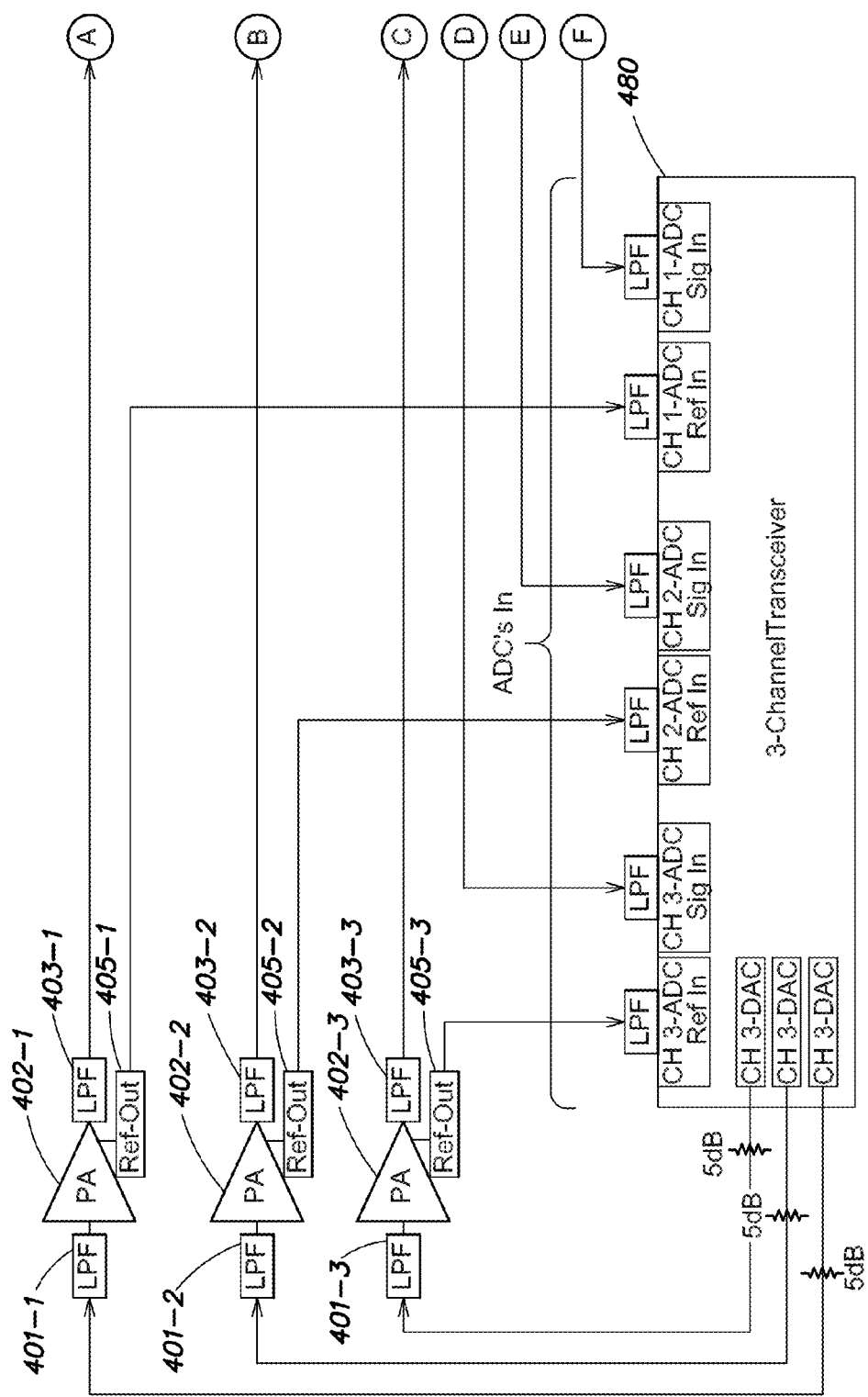
FIGS. 12A and 12B show a high level block diagram of an NQR system using conductive wire radiators and a directional coupler.
Figure 12B:
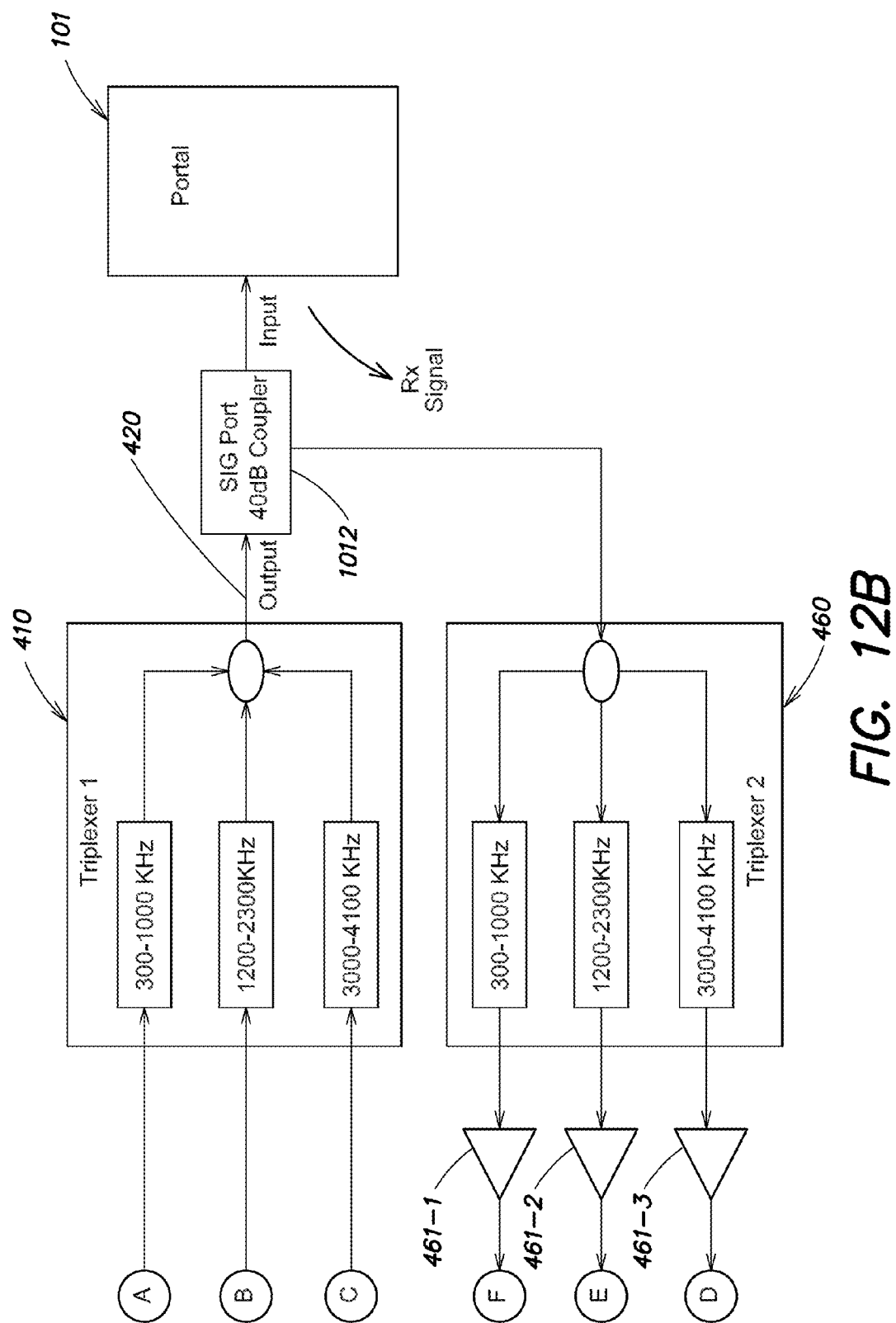

FIGS. 12A and 12B are a block diagram view of the system 100 portal 101. As in the embodiments described above in connection with FIGS. 4A and 4B and 6A and 6B the system 100 electronics including the PC (not shown) and associated digital and analog circuits, amplifiers, couplers, filters, DACs, ADCs, triplexer, etc. The portal 101 is defined by one or more conductive surfaces are arranged to define a space that is to be monitored. Here, wire conductors or slabs are disposed within the portal, adjacent selected ones of the conductive surfaces, and used as both transmit and receive radiators. A four part directional coupler 1012 is dispersed between the transmitter, receiver, and radiator(s).

FIG. 13 shows a person 220 standing in the portal 101 carrying a material 230 of interest at a height, h, off the portal floor.

The signal emitted by the material of interest 230 due to the nuclear quadrupole resonance effect, detected as the receiver signal at the (SIG) port, has both an amplitude and phase component. When that phase is measured relative to the reference (REF) waveform (e.g., from directional coupler 1012), it provides a measure of the vertical location of the explosive in the portal since the portal fields are traveling wave fields in the vertical direction and the signals are stimulated emissions from the explosive.

Figure 14:
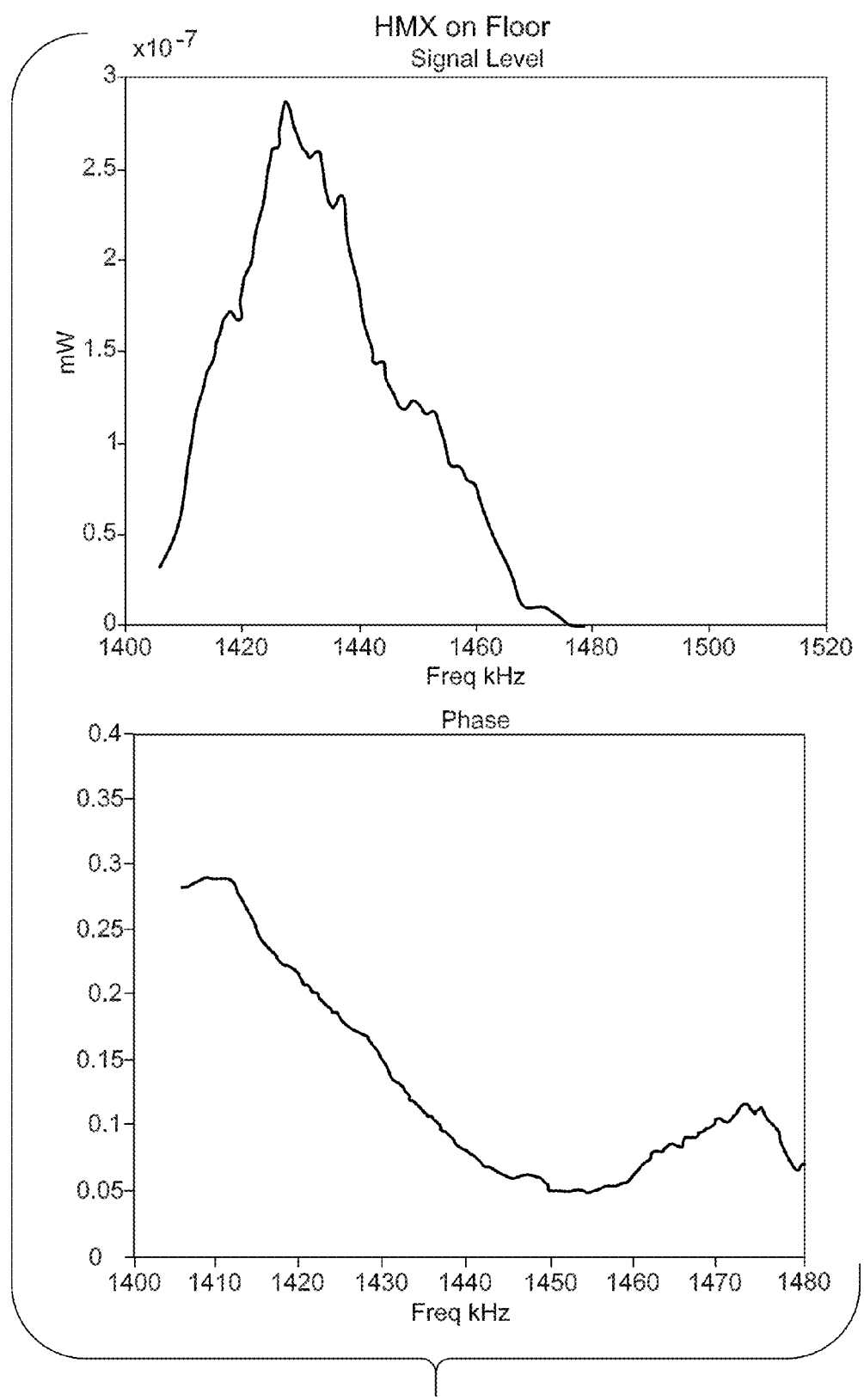
FIG. 14 is the resulting response signal for HMX located on the portal floor.
Figure 15:
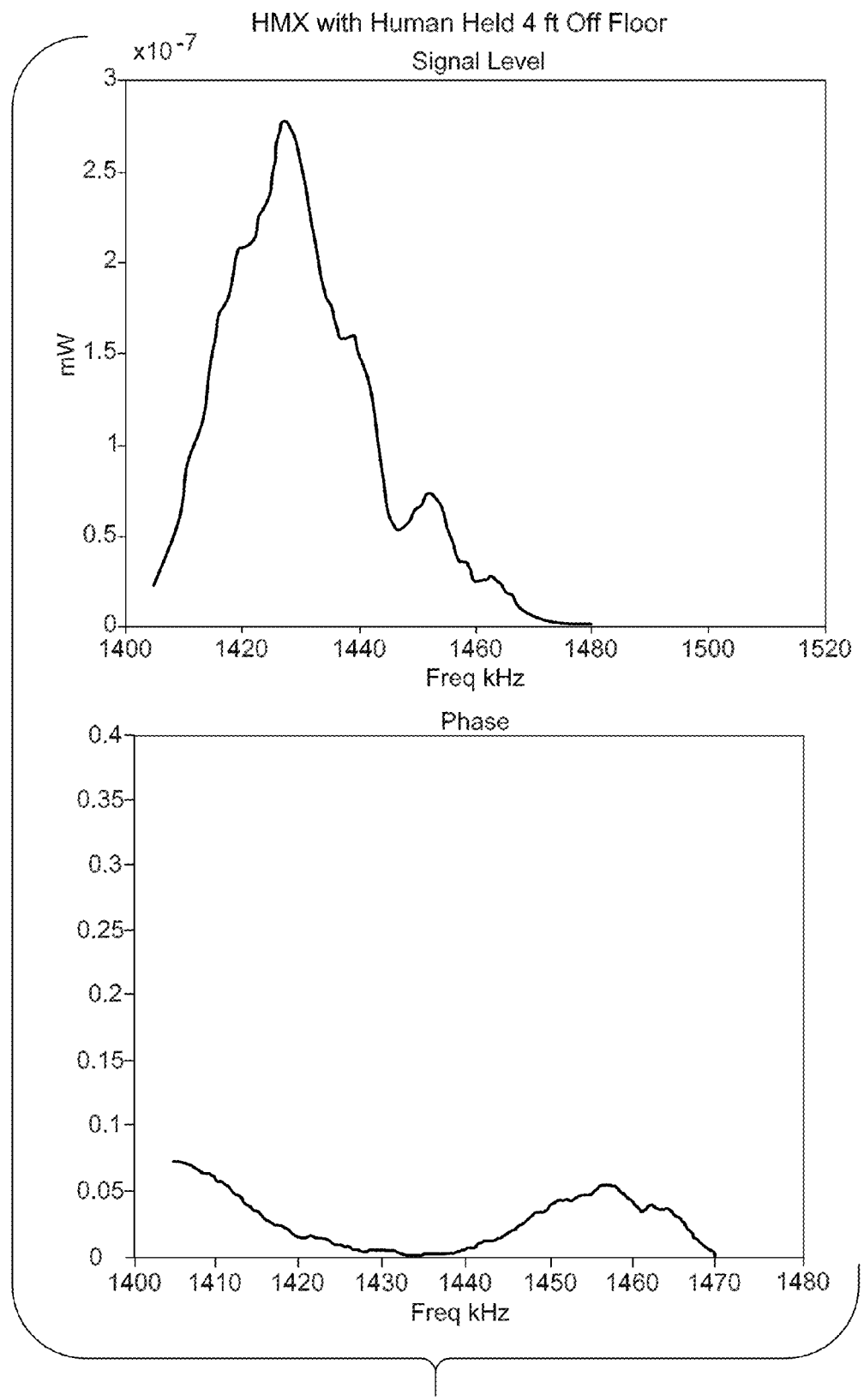
FIG. 15 is the response for HMX being carried by a person 4 feet off the floor.

An example of this phenomenon is shown in the FIGS. 14 and 15. FIG. 14 shows the phase and amplitude of the response to a material of interest, HMX, having an expected resonance at approximately 1440 kHz. The response was measured for a case of 5 grams of HMX placed on the metal floor of the portal.

FIG. 15 shows the phase and amplitude of the same 5 grams of HMX material held at a height, h, of 4 feet by a human being standing in the middle of the portal 101. Thus it can be seen that comparing the relative phases of the responses can provide an indication of the location of the material within the portal, with the phase being a function of distance from the floor. In this example for 1440 kHz and a 4 foot height, there is a phase difference of about 0.07 radian or 4 degrees. The theoretical phase shift relative to the floor, assuming an 8 foot extra path length is 4.15 degrees. The error in location can be determined to be about 1.8 inches.

The phase difference is not an absolute indication of the vertical location above the floor, but rather is also a function of frequency. Thus the conversion from a Phase measurement to a height measurement should therefore be adapted for each resonance frequency of interest. The result can be a phase-to-height conversion factor for each frequency, or a table of converted factors to be applied to the resulting measured phases.

Once the height (or other location) of the material on a person within the portal is determined, the location information can be displayed to the operator of the system or the information can be passed to other personnel for further decision making.

9. Multiple Single Loop Radiators

Figure 16:
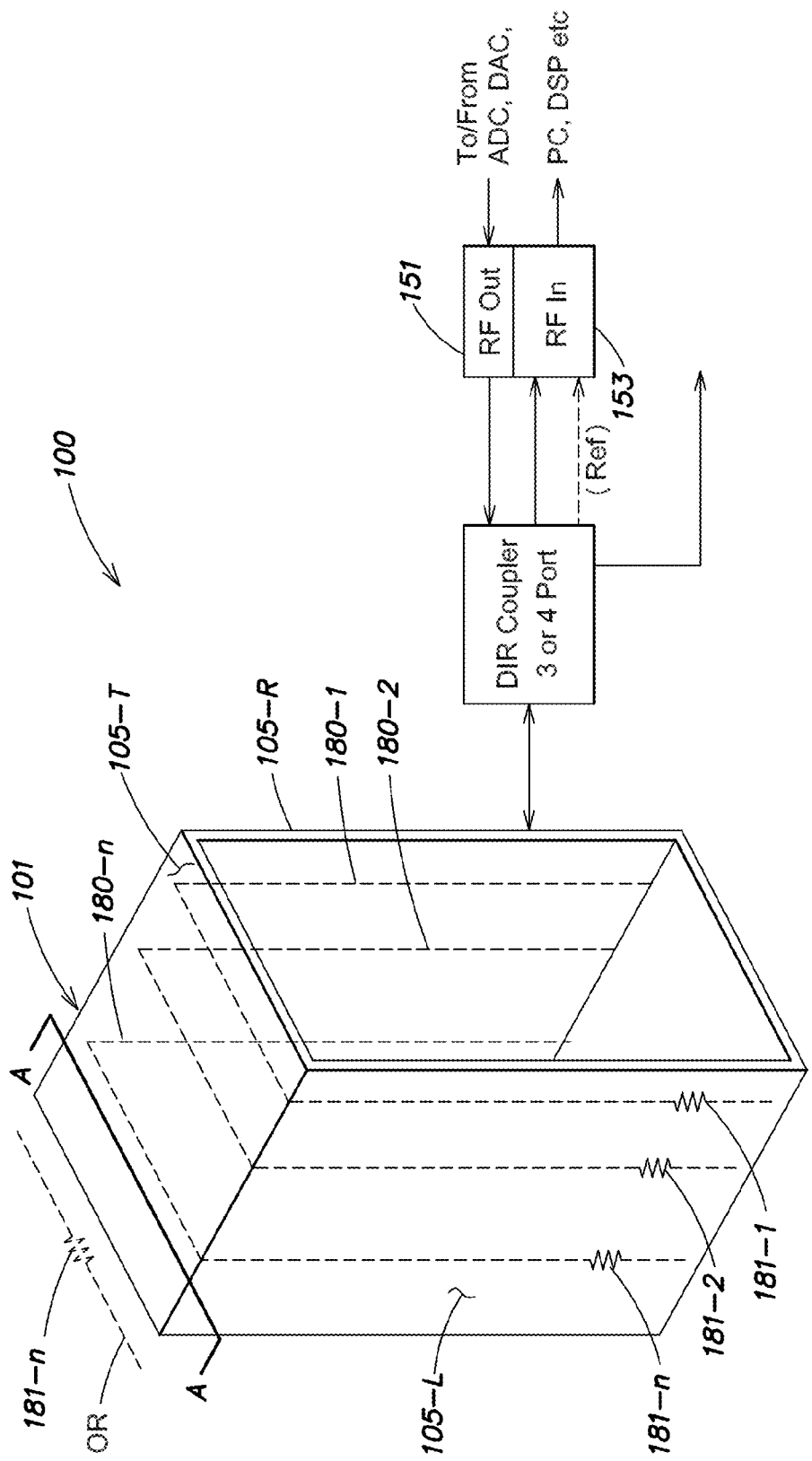
FIG. 16 is a diagram illustrating a set of single wire conductor radiators that run along a first side, top, and opposite side of a portal, each terminating in a resistance adjacent the opposite side.

FIG. 16 shows yet another arrangement of conductors with respect to portal 101. In this embodiment, conductors are formed from a set of individual wires 180-1, 180-2, . . . , 180-n. Each individual conductor is a length that runs adjacent several surfaces of the portal internal to it. For example, a first conductor 180-1 is coupled to the transceiver circuits at a location adjacent the floor and one of the portal walls such as right side wall 105-L. The conductor 180-1 is then run along top wall 105-T to the opposite portal wall such as left side wall 105-L. This continuous single conductor is terminated in a single termination impedance 181-1 located near the floor. In an optional arrangement, the impedences may be located in the middle of conductor 180 such as near the portal roof Similar conductors 180-2, . . . , 180-n are disposed inside the walls of portal 101, but spaced at increasing depths from the portal entrance, such that conductor 180-n is the farthest away from the entrance. In one embodiment, the conductors 180 may be axially aligned with one another and positioned with respect to the portal such that each conductor 180 is disposed in a plane parallel to the portal entrance (eg., plane A-A).

The system 100 otherwise takes the form of any of the other systems previously described and includes a coupler, RFin and RFout circuits, A/D converters, D/A converters, the PC and DSP(s).

In this arrangement, the single termination resistance for each conductor 180 eliminates the need for balanced transmission lines used in other embodiments.

An embodiment with multiple such conductors disposed at different spacings from the portal entrance provides further information as to the position of materials within the portal. For example, if the response received from conductor 180-2 is of greater strength than that received from conductor 180-1 or 180-n, the DSP or PC can conclude the material's depth within the portal is closest to the plane defined by conductor 180-2.

It will now be understood that by combing the various techniques described above, the system can determine the position of material of interest in all three dimensions within the portal—height from the floor (as per the determination of phase is information as discussed in connection with FIG. 13), right to left (as per the discussion of FIG. 4D), and depth (as per FIG. 16).

What is claimed is:

1. A system comprising:
  a portal including at least three conductive surfaces including a pair of left and right opposing side walls and a roof disposed between the left and right side walls to define a portal space;
  a radio frequency chirp transmitter, to emit a time varying electromagnetic field that includes a chirp signal into the portal space;
  a radio frequency chirp receiver for detecting coherent emissions from materials disposed within the portal space that are responsive to the time varying electromagnetic field;
  a transmit radiator structure coupled to the chirp transmitter and further comprising a conductor running along, inside of, and adjacent to the left side, roof, and right side of the portal; and a receive radiator structure coupled to the radio frequency chirp receiver, the receive radiator structure disposed within the portal and separate from the transmit radiator structure.

2. The system of claim 1 where the transmit radiator structure is a conductive surface formed of aluminum.

3. The system of claim 1 wherein the transmit radiator structure is a slab radiator comprising a left, top, and right conductive slab surface, with each slab surface disposed adjacent a respective one of the left side, top, and right side of the portal, the conductive slab surfaces having a width of more than ⅓ of a width of at least one side of the portal.

4. The system of claim 3 wherein an impedance of the transmit radiator structure is 12.5 ohms.

5. The system of claim 3 further comprising one or more shunt capacitors disposed between a respective one of the left, top, or right slab surfaces and the left portal side, right portal side or roof.

6. The system of claim 3 wherein the transmit structure further comprises:
a balun disposed between the left slab surface and right slab surface at one end thereof; and
a resistor disposed between the left slab surface and right slab surface at an opposing end thereof.

7. The system of claim 1 wherein receive structure further comprises a resistive coupler.

8. The system of claim 3 wherein receive structure further comprises:
a stripline conductor disposed within the portal adjacent and running inboard of one of the left or right side slab radiators from a location near a bottom of the portal to a position near the roof;
a terminating resistor connected to one end of the stripline conductor near the bottom of the portal; and
a coaxial cable connected to an opposite end of the stripline conductor.

9. The system of claim 8 additionally comprising:
a second stripline conductor disposed adjacent another one of the left or right side slab radiators.

10. The system of claim 1 additionally comprising a directional coupler disposed between a transmit signal path and receive signal path and biased to provide magnetic field amplification.

11. The system of claim 1 further comprising:
a four port directional coupler including:
a series inductive and/or parallel capacitive coupling between an input port and an output port;
a first resistive coupling between the input port and a reference port; and
a second resistive coupling between the output port and a signal port.

12. A system comprising:
a portal including at least three conductive surfaces including a pair of left and right opposing side walls and a roof disposed between the left and right side walls to define a portal space;
at least one conductor disposed within the space adjacent the conductive surface;
a radio frequency chirp transmitter, to emit a time varying electromagnetic field that includes a chirp signal into the portal space, the radio frequency chirp generating a plurality of time varying linear chirp signals, each chirp signal including one or more selected radio frequencies depending on Nuclear Quadrupole Resonance (NQR) frequencies of the materials of interest, each material of interest having more than one NQR resonance frequency;
a coupler, for coupling the radio frequency chirp transmitter to the conductor; and
a processor, for controlling the radio frequency chirp transmitter to generate, at a given time, multiple simultaneous chirp signals, but constrained such that only one of the multiple NQR resonance frequencies of interest for a specific material is generated at a given time, and further such that chirps corresponding to resonance frequencies of materials other than the specific material are generated at the given time.

13. The system of claim 12 additionally comprising
multiple digital to analog converters, connect to be controlled by the processor, and each generating a selected one of the multiple chirp signals.

14. The system of claim 12 wherein three simultaneous chirp signals are composed to excite NQR resonances in at least six different materials of interest.

15. The system of claim 14 wherein a first chirp signal ranges from 360 to 940 kHz, a second chirp signal ranges from 1370 to 2030 khz, and a third chirp signal ranges from 3300 to 3830 khz.

16. The system of claim 12 additionally comprising:
six digital to analog converters (DACs), controlled by the processor to generate six simultaneous chirp signals;
three diplexers, each coupled to a selected pair of the DACs, and each diplexer having a pair of bandpass filters to provide three diplexer output signals;
a triplexer, coupled to the three diplexers, and having three bandpass filters, to provide a combined broadband chirp signal to the coupler.

17. The system of claim 16 additionally wherein:
a first diplexer comprises bandpass filters having passbands from 270 to 440 khz and from 460 to 530 khz;
a second diplexer comprises bandpass filters having passbands from 670 to 785 khz and from 815 to 1615 khz; and
a third diplexer comprises bandpass filters having passbands from 1735 to 2770 khz and from 3360 to 4690 khz.

18. The system of claim 17 wherein the triplexer comprises:
a first bandpass filter having a passband from 270 to 550 khz;
a second bandpass filter having a passband form 650 to 1625 khz;
a third bandpass filter having a passband from 1700 to 4700 khz.

19. A system comprising:
at least a left side and right side conductive planar surface spaced apart from one another and defining a portal;
at least one conductor disposed adjacent at least one conductive surface;
a radio frequency transmitter, to generate a plurality of time varying electromagnetic chirp signals at selected power levels and selected frequencies;
a radio frequency receiver, for detecting signals resulting from Nuclear Quadrupole Resonance (NQR) stimulated by the radio frequency transmitter in a substance located within the portal;
a directional coupler coupled to the radio frequency transmitter, to the at least one conductor, and to the radio frequency receiver, to provide a reference signal; and
a processor, for further processing the detected NQR signals and the reference signal to determine a relative position of the substance within the portal.

20. The system of claim 19 wherein the processor determines a relative phase difference between the detected NQR signals and the reference signal indicates a relative height of the substance within the portal.

21. The system of claim 19 additionally comprising:
at least one other conductor disposed adjacent another conductive surface such that each conductive surface has at least one adjacent conductor;
the coupler is coupled to both conductors; and
wherein the processor determines a relative signal strength between NQR response signals received on the two conductors to further determine a relative left and right side position of the substance.

22. The system of claim 19 additionally comprising:
a plurality of conductors disposed adjacent at least a given one of either the left or right side surfaces;
each of the plurality of conductors coupled to the coupler; and
wherein the processor further compares a relative signal strength between NQR signals received from the plurality of conductors to determines a relative depth of the substance within the portal.

23. The system of claim 19 additionally comprising:
a plurality of conductors disposed adjacent each of the left and right side surfaces;
each of the plurality of conductors coupled to the coupler; and
wherein the processor further compares a relative phase and relative signal strength between a reference signal and NQR signals received from the plurality of conductors and among the NQR signals to determine a relative height, depth, and side to side position of the substance within the portal.

24. A system comprising:
a portal including at least three conductive surfaces including a pair of left and right side walls and a roof disposed between the left and right side walls to define a portal space;
a radio frequency chirp transmitter, to emit a time varying electromagnetic field that includes a chirp signal into the portal space;
a radio frequency chirp receiver for detecting coherent emissions from materials disposed within the portal space, the materials emitting a nuclear quadrupole resonance responsive to the time varying electromagnetic field;
a conductive wire having one end coupled to at least one of the chirp transmitter and/or receiver, and another end coupled to a terminating resistor, the conductive wire running along and adjacent to the left side, roof, and right side of the portal.

25. The system of claim 24 further comprising:
a plurality of conductive wires running along and adjacent to the left side, roof,
and right side of the portal, each coupled to a respective terminating resistor.

* * * * *